(12) United States Patent
Henderson et al.

(10) Patent No.: US 8,403,965 B2
(45) Date of Patent: Mar. 26, 2013

(54) VERTEBRA ATTACHMENT METHOD AND SYSTEM

(75) Inventors: Fraser Cummins Henderson, Upper Marlboro, MD (US); John W. Newman, Newtown Square, PA (US)

(73) Assignee: Polaris Biotechnology, Inc., Newtown Square, PA (US)

( * ) Notice: Subject to any disclaimer, the term of this patent is extended or adjusted under 35 U.S.C. 154(b) by 933 days.

(21) Appl. No.: 12/234,521

(22) Filed: Sep. 19, 2008

(65) Prior Publication Data

US 2009/0018584 A1    Jan. 15, 2009

Related U.S. Application Data

(63) Continuation-in-part of application No. 11/832,643, filed on Aug. 1, 2007, which is a continuation-in-part of application No. 11/832,646, filed on Aug. 1, 2007.

(60) Provisional application No. 60/987,567, filed on Nov. 13, 2007, provisional application No. 60/887,022, filed on Jan. 29, 2007.

(51) Int. Cl.
*A61B 17/80* (2006.01)

(52) U.S. Cl. .................................. 606/280; 606/903

(58) Field of Classification Search ............... 606/246, 606/257, 250, 280, 902, 903
See application file for complete search history.

(56) References Cited

U.S. PATENT DOCUMENTS

| | | |
|---|---|---|
| 1,135,699 A | 4/1915 | Knauber |
| 1,739,009 A | 12/1929 | Lorber |
| 1,750,769 A | 3/1930 | Austin |
| 2,669,405 A | 2/1954 | Donnelly |
| 3,073,022 A | 1/1963 | Bush et al. |
| 4,456,005 A | 6/1984 | Lichty |
| 4,653,481 A | 3/1987 | Howland et al. |
| 4,655,199 A | 4/1987 | Steffee |
| 4,762,122 A | 8/1988 | Slocum |
| 4,790,702 A | 12/1988 | Maganias |
| 4,800,874 A | 1/1989 | David et al. |
| 4,805,602 A | 2/1989 | Puno et al. |
| 5,030,220 A | 7/1991 | Howland |
| 5,034,011 A | 7/1991 | Howland |
| 5,129,900 A | 7/1992 | Asher et al. |
| 5,133,716 A | 7/1992 | Plaza |
| 5,176,680 A | 1/1993 | Vignaud et al. |
| 5,269,784 A | 12/1993 | Mast |
| 5,360,429 A | 11/1994 | Jeanson et al. |
| 5,470,333 A | 11/1995 | Ray |
| 5,507,745 A | 4/1996 | Logroscino et al. |

(Continued)

FOREIGN PATENT DOCUMENTS

| | | |
|---|---|---|
| DE | 102004061280 A1 | 6/2006 |
| WO | 20040069038 | 8/2004 |

(Continued)

OTHER PUBLICATIONS

Corbett, J. J., et al., "'Sneeze syncope,' basilar invagination and Arnold-Chiari type 1 malformation", J Neurol, Neurosurg, and Psych, 1976; 39: 381-384.

(Continued)

*Primary Examiner* — Kevin T Truong
*Assistant Examiner* — Christian Sevilla
(74) *Attorney, Agent, or Firm* — The Patentwise Group, LLC

(57) ABSTRACT

A vertebral attachment method and system that minimizes or eliminates the risk of severing, compressing, impinging or otherwise injuring the vertebral artery vertebral vein, spinal nerve roots and/or spinal cord. The system includes at least one plate that may be anchored to a posterior region of a vertebra using at least one clamp and fastener. The system may be specifically designed to retain a portion of the posterior region of the vertebra.

16 Claims, 20 Drawing Sheets

U.S. PATENT DOCUMENTS

| | | | |
|---|---|---|---|
| 5,545,164 A | 8/1996 | Howland | |
| 5,545,228 A | 8/1996 | Kambin | |
| 5,611,354 A | 3/1997 | Alleyne | |
| 5,643,261 A | 7/1997 | Schafer et al. | |
| 5,653,710 A | 8/1997 | Harle | |
| 5,733,285 A | 3/1998 | Errico et al. | |
| 5,800,435 A | 9/1998 | Errico et al. | |
| 5,968,047 A | 10/1999 | Reed | |
| 6,039,738 A | 3/2000 | Sanders et al. | |
| 6,056,753 A | 5/2000 | Jackson | |
| 6,059,786 A | 5/2000 | Jackson | |
| 6,080,579 A | 6/2000 | Hanley, Jr. et al. | |
| 6,102,913 A | 8/2000 | Jackson | |
| 6,125,526 A | 10/2000 | Wierzchon | |
| 6,129,728 A | 10/2000 | Schumacher et al. | |
| 6,129,730 A | 10/2000 | Bono et al. | |
| 6,146,382 A | 11/2000 | Hurlbert | |
| 6,179,841 B1 | 1/2001 | Jackson | |
| 6,193,719 B1 | 2/2001 | Gournay et al. | |
| 6,221,073 B1 | 4/2001 | Weiss et al. | |
| 6,224,596 B1 | 5/2001 | Jackson | |
| 6,238,396 B1 | 5/2001 | Lombardo | |
| 6,319,254 B1 | 11/2001 | Giet et al. | |
| 6,325,803 B1 | 12/2001 | Schumacher et al. | |
| 6,355,043 B1 | 3/2002 | Adam | |
| 6,423,067 B1 | 7/2002 | Eisermann | |
| 6,454,768 B1 | 9/2002 | Jackson | |
| 6,454,772 B1 | 9/2002 | Jackson | |
| 6,520,990 B1 | 2/2003 | Ray | |
| 6,524,315 B1 | 2/2003 | Selvitelli et al. | |
| 6,547,790 B2 | 4/2003 | Harkey, III et al. | |
| 6,565,566 B1 | 5/2003 | Wagner et al. | |
| 6,623,486 B1 | 9/2003 | Weaver et al. | |
| 6,726,687 B2* | 4/2004 | Jackson | 606/916 |
| 6,761,721 B2 | 7/2004 | Burgess et al. | |
| 6,783,527 B2 | 8/2004 | Drewry et al. | |
| 6,902,565 B2 | 6/2005 | Berger et al. | |
| 6,928,900 B2 | 8/2005 | Dall et al. | |
| 6,997,927 B2 | 2/2006 | Jackson | |
| 7,018,379 B2 | 3/2006 | Drewry et al. | |
| 7,033,358 B2 | 4/2006 | Taylor et al. | |
| 7,052,499 B2 | 5/2006 | Steger et al. | |
| 7,131,303 B1 | 11/2006 | Champaigne | |
| 7,213,999 B2 | 5/2007 | Haas | |
| 7,235,079 B2 | 6/2007 | Jensen et al. | |
| 7,250,052 B2 | 7/2007 | Landry et al. | |
| 7,303,563 B2 | 12/2007 | Poyner et al. | |
| 7,354,442 B2 | 4/2008 | Sasso et al. | |
| 7,537,596 B2 | 5/2009 | Jensen | |
| 7,635,365 B2* | 12/2009 | Ellis et al. | 606/71 |
| 2001/0020168 A1 | 9/2001 | Hermann et al. | |
| 2002/0120268 A1 | 8/2002 | Berger | |
| 2003/0153913 A1 | 8/2003 | Altarac et al. | |
| 2003/0176863 A1 | 9/2003 | Ueyama et al. | |
| 2004/0030388 A1 | 2/2004 | Null et al. | |
| 2004/0153070 A1 | 8/2004 | Barker et al. | |
| 2005/0038438 A1 | 2/2005 | Anderson et al. | |
| 2005/0080417 A1 | 4/2005 | Alexis et al. | |
| 2005/0124994 A1 | 6/2005 | Berger et al. | |
| 2005/0143737 A1 | 6/2005 | Pafford et al. | |
| 2005/0159750 A1 | 7/2005 | Doherty | |
| 2005/0216001 A1 | 9/2005 | David | |
| 2005/0283153 A1 | 12/2005 | Poyner et al. | |
| 2005/0283248 A1 | 12/2005 | Gordon et al. | |
| 2005/0288669 A1 | 12/2005 | Abdou | |
| 2006/0004363 A1 | 1/2006 | Brockmeyer et al. | |
| 2006/0058790 A1* | 3/2006 | Carl et al. | 606/61 |
| 2006/0079895 A1 | 4/2006 | McLeer | |
| 2006/0173543 A1 | 8/2006 | Brau et al. | |
| 2006/0217710 A1 | 9/2006 | Abdou | |
| 2006/0224242 A1 | 10/2006 | Swords et al. | |
| 2006/0264946 A1 | 11/2006 | Young | |
| 2006/0264948 A1 | 11/2006 | Williams | |
| 2006/0293660 A1 | 12/2006 | Lewis et al. | |
| 2007/0118121 A1 | 5/2007 | Purcell et al. | |
| 2007/0219554 A1 | 9/2007 | Landry et al. | |
| 2007/0270840 A1 | 11/2007 | Chin et al. | |
| 2008/0039843 A1 | 2/2008 | Abdou | |
| 2008/0045957 A1 | 2/2008 | Landry et al. | |
| 2008/0086124 A1 | 4/2008 | Forton et al. | |
| 2008/0125781 A1 | 5/2008 | Hoffman et al. | |
| 2008/0200953 A1 | 8/2008 | Reiley et al. | |
| 2008/0234755 A1 | 9/2008 | Henderson, Sr. et al. | |
| 2008/0234766 A1 | 9/2008 | Henderson, Sr. et al. | |
| 2009/0036894 A1 | 2/2009 | Henderson, Sr. et al. | |
| 2009/0177230 A1 | 7/2009 | Henderson, Sr. et al. | |
| 2010/0152575 A1 | 6/2010 | Henderson et al. | |

FOREIGN PATENT DOCUMENTS

| | | |
|---|---|---|
| WO | 20070005561 | 1/2007 |
| WO | 20070044716 | 4/2007 |
| WO | 2010002409 | 1/2010 |

OTHER PUBLICATIONS

Geddes, J. F., et al., "Neuropathology of inflicted head injury in children. II: Microscopic brain injury in infants", Brain, 2001: 124: 1299-1306.

Goel, Atul, "Treatment of basilar invaginations by atlantoaxial joint distraction and direct lateral mass fixation", J Neurosurg, 2004. 3: 281-286.

Goel, Atul, et al., "Craniovertebral Junction Realignment for the Treatment of Basilar Invagination With Syringomyelia: Preliminary Report of 12 Cases", Neurol Med Chir, 2005. 45: 512-518.

Grabb, Paul A., et al., "Ventral Brain Stem Compression in Pediatric and Young Adult Patients with Chiari 1 Malformations", Neurosurgery, 1999. 44(3): 520-528.

Kim, Louis J., et al., "Treatment of basilar invagination associated with Chiari 1 malformations in the pediatric population: cervical reduction and posterior occipitocervical fusion", J Neurosurg, 2004. 101: 189-195.

Levine, David N., "Pathogenesis of cervical spondylotic myelopathy", J Neurol, Neurosrug, and Psych, 1997. 62: 334-340.

Phillips, Douglas G., "Surgical treatment of myelopathy with cervical spondylosis", J Neurol, Neurosrug, and Psych, 1973. 36: 879-884.

Rossignol, Daniel A., et al., "The effects on hyperbaric oxygen therapy on oxidative stress, inflammation, and symptoms in children with autism: an open-label pilot study", BMC Pediatrics, 2007. 7: 36.

Ryken, Timothy C., et al., "Cervicomedullary compression in achondroplasia", J Neurosurg, 1994. 81: 43-48.

Stradling, J R, et al., "Changes in ventilation and its components in normal subjects during sleep", Thorax, 1985. 40: 364-370.

Tassanwipas, A, et al., "Magnetic resonance imaging study of the craniocervical junction", J Ortho Surg, 2005. 13(3): 228-231.

Aman, Michael G., et al., "The Aberrant Behavior Checklist: A Behavior Rating Scale for the Assessment of Treatment Effects", Am J Ment Defic, 1985: 89(5): 485-491.

Aman, Michael G., et al., "Psychometric Characteristics of the Aberrant Behavior Checklist", Am J Ment Defic, 1985: 89(5): 492-502.

Arundine, Mark, et al., "Vulnerability of Central Neurons to Secondary Insults after In Vitro Mechanical Stretch", J Neurosci, 2004. 24(37): 8106-8123.

Bain, Allison C., et al., "Tissue-Level Thresholds for Axonal Damage in an Experimental Model of Central Nervous System White Matter Injury", J Biomech Eng, 2000. 122: 615-622.

Bilston, Lynne E., et al., "The Mechanical Properties of the Human Cervical Spinal Cord In Vitro", Ann Biomed Eng, 1996. 24: 67-74.

Breig, A., "Overstretching of and Circumscribed Pathological Tension in the Spinal Cord—A Basic Cause of Symptoms in Cord Disorders", J Biomech, 1970. 3: 7-9.

Sawin, Paul D., et al., "Basilar invagination in osteogenesis imperfecta and related osteochondrodysplasias: medical and surgical management", J Neurosurg, 1997. 86: 950-960.

Brill, Charles B., et al., "Chiari I Malformation: Association With Seizures and Developmental Disabilities", J Child Neurog, 1997. 12(2): 101-106.

Brooks, Arthur L., et al., "Atlanto-axial arthrodesis by the wedge compression method", J Bone Joint Surg Am, 1978. 60(3): 279-284.

Bunge, Richard P., et al., "Observations on the Pathology of Human Spinal Cord Injury. A Review and Classification of 22 New Cases with Details from a Case of Chronic Cord Compression with Extensive Focal Demyelination", Adv Neurol, 1993. 59: 75-89.

Bunge, Richard P., et al., "Observations on the Pathology of Several Types of Human Spinal Cord Injury, with Emphasis on the Astrocyte Response to Penetrating Injuries", Adv Neurol, 1997. 72: 305-315.

Charman, Tony, et al., "Practitioner Review: Diagnosis of autism spectrum disorder in 2- and 3-year-old children", J Child Psychol Psychiatry, 2002. 43(3): 289-305.

Coyne, Terry J., et al., "C1-C2 Posterior Cervical Fusion: Long-term Evaluation of Results and Efficacy", Neurosurgery, 1995. 37(4): 688-693.

Crowe, Maria J., et al., "Apoptosis and delayed degeneration after spinal cord injury in rats and monkeys", Nat Med, (1): 73-76.

Cushing, K E, et al., "Tethering of the vertebral artery in the congenital arcuate foramen of the atlas vertebra: a possible cause of vertebral artery dissection in children", Dev Med Child Neurol, 2001. 43(7): 491-496.

Dickman, Curtis A., et al., "Posterior C1-C2 Transarticular Screw Fixation for Atlantoaxial Arthrodesis", Neurosurgery, 1998. 43(2): 275-280.

Dyste, Gregg N., et al., "Presentation and Management of Pediatric Chiari Malformations without Myelodysplasia", Neurosurgery, 1988. 23(5): 589-597.

Eleraky, Mohammed Aly, et al., "Posterior atlantoaxial facet screw fixation in rheumatoid arthritis", J Neurosurg, 1998. 89: 8-12.

Fein, Deborah, et al., "Clinical Correlates of Brainstem Dysfunction in Autistic Children", J Autism and Dev Disorders, 1981. 11(3): 303-315.

Fombonne, Eric, "The epidemiology of autism: a review", Psych Med, 1999. 29: 769-786.

Fombonne, Eric, "The Prevalence of Autism", JAMA, 2003. 289(1): 87-89.

Fombonne, Eric, et al., "MMR and autistic enterocolitis: consistent epidemiological failure to find an association", Mol Psychiatry, 2003. 8: 133-134.

Gaffney, Gary R., et al., "Morphological Evidence for Brainstem Involvement in Infantile Autism", Biol Psychiatry, 1988. 24: 578-586.

Galbraith, J. A., et al., "Mechanical and Electrical Responses of the Squid Giant Axon to Simple Elongation", J Biomech Eng, 1993. 115: 13-22.

Gallie, W. E., "Fractures and Dislocations of the Cervical Spine", Am J Surg, 1939. 46: 495-499.

Geddes, J. F., et al., "Traumatic axonal injury: practical issues for diagnosis in medicolegal cases", Neuorpath Appl Neurobio, 2000. 26: 105-116.

Grob, Dieter, et al., "Biomechanical Evaluation of Four Different Posterior Atlantoaxial Fixation Techniques", Spine, 1992. 17(5): 480-490.

Haid, Jr., Regis W., et al., "C1-C2 Transarticular Screw Fixation for Atlantoaxial Instability: A 6-year Experience", Neurosurgery, 2001. 49(1): 65-70.

Harms, Jurgen, et al., "Posterior C1-C2 Fusion With Polyaxial Screw and Rod Fixation", Spine, 2001. 26(22): 2467-2471.

Hasan, Mahdi, et al., "Posterolateral tunnels and ponticuli in human atlas vertebrae", J Anat, 2001. 199(3): 339-343.

Henderson, Fraser C., et al., "Neuropathology of the brainstem and spinal cord in end stage rheumatoid arthritis: implications for treatment.", Ann Rheum Dis, 1993. 52(9): 629-637.

Henderson, Fraser C., et al., "Stretch-Associated Injury in Cervical Spondylotic Myelopathy: New Concept and Review", Neurosurgery, 2005. 56(5): 1101-1113.

Henriques, Thomas, et al., "Biomechanical Comparison of Five Different Atlantoaxial Posterior Fixation Techniques", Spine, 2000. 25(22): 2877-2883.

Holness, Renn O., et al., "Posterior Stabilization with an Interlaminar Clamp in Cervical Injuries: Technical Note and Review of the Long Term Experience with the Method", Neurosurgery, 1984. 14(3): 318-322.

Hong, Xia, et al., "Posterior Screw Placement on the Lateral Mass of Atlas: An Anatomic Study", Spine, 2004. 29(5): 500-503.

Howlin, Patricia, et al., "Diagnosis in Autism: A Survey of Over 1200 Patients in the UK", autism, 1997. 1(2): 135-162.

Ichihara, Kazuhiko, et al., "Gray Matter of the Bovine Cervical Spinal Cord is Mechanically More Rigid and Fragile than the White Matter", J Neurotrama, 2001. 18(3): 361-367.

Ichihara, Kazuhiko, et al., "Mechanism of the spinal cord injury and the cervical spondylotic myelopathy: new approach based on the mechanical features of the spinal cord white and gray matter", J Neurosurg: Spine, 2003. 99: 278-285.

Iwasaki, Motoki, et al., "Cervical Kyphosis: Predictive Factors for Progression of Kyphosis and Myelopathy", Spine, 2002. 27(13): 1419-1425.

Iwata, Akira, et al., "Traumatic Axonal Injury Induces Proteolytic Cleavage of the Voltage-Gated Sodium Channels Modulated by Tetrodotoxin and Protease Inhibitors", J Neuroscience, 2004. 24(19): 4605-4613.

Jafari, Saeed S., et al., "Axonal Cytoskeletal Changes After Nondisruptive Axonal Inury. II. Intermediate Sized Axons", J Neurotrama, 1998. 15(11): 955-966.

Johansson, Maria, et al., "Autistic spectrum disorders in Mobius sequence: a comprehensive study of 25 individuals", Dev Med Child Neurology, 2001. 43: 338-345.

Kitahara, Yukio, et al., "Effect of Spinal Cord Stretching due to Head Flexion on Intramedullary Pressure", Neurol Med Chir (Tokyo), 1995. 35: 285-288.

Kocak, Ayhan, et al. "A New Model for Tethered Cord Syndrome: A Biochemical, Electrophysiological, and Electron Microscopic Study", Pediatr Neurosurg, 1997. 26(3): 120-126.

Le Couteur, Ann, et al., "National Autism Plan for Children (NAPC)", National Initiative for Autism: Screening and Assessment (NIASA), 2003.

Lusardi, Theresa A., et al., "The separate roles of calcium and mechanical forces in mediating cell death in mechanically injured neurons", Biorheology, 2003. 40: 401-409.

Magerl, F., et al., "Stable Posterior Fusion of the Atlas and Axis by Transarticular Screw Fixation", Cervical Spine, 1987. 1: 322-327.

Maxwell, William L., et al., "Post-Acute Alterations in the Axonal Cytoskeleton after Traumatic Axonal Injury", J Neurotrama, 2003. 20(2): 151-168.

Menezes, Arnold H., et al., "Transoral-transpharyngeal approach to the anterior craniocervical junction. Ten-year experience with 72 patients.", J Neurosurg, 1988. 69: 895-903.

Milhorat, Thomas H., et al., "Chiari I Malformation Redefined: Clinical and Radiographic Findings for 364 Symptomatic Patients", Neurosurgery, 1999. 44(5): 1005-1017.

Naderi, Sait, et al., "Biomechanical Comparison of C1-C2 Posterior Fixations: Cable, Graft, and Screw Combinations", Spine, 1998; 23(18): 1946-1955.

Osterling, Julie, et al., "Early Recognition of Children with Autism: A Study of First Birthday Home Videotapes", J Autism Dev Disorders, 1994: 24(3): 247-257.

Pang, Dachling, et al., "Tethered cord syndrome in adults", J Neurosurg, 1982. 57(1): 32-47.

Piek, Jan P., et al., "Sensory-motor deficits in children with developmental coordination disorder, attention deficit hyperactivity disorder and autistic disorder", Hum Move Science, 2004. 23: 475-488.

Povlishock, John T., "Traumatically Induced Axonal Injury: Pathogenesis and Pathobiological Implications" Brain Pathology, 1992. 2(1): 1-12.

Povlishock, John T., et al., "The Pathobiology of Traumatically Induced Axonal Injury in Animals and Humans: A Review of Current Thoughts", J Neurotrama, 1995. 12(4): 555-564.

Rapin, Isabelle, "Appropriate investigations for clinical care versus research in children with autism", Brain & Develop, 1999. 21: 152-156.

Reich, D.S., et al., "Quantitative Characterization of the Corticospinal Tract at 3T", Am J Neuroradiol, 2006. 27: 2168-2178.

Resnick, Daniel K., et al., "Anatomic Suitability of the C1-C2 Complex for Pedicle Screw Fixation", Spine, 2002. 27 (14): 1494-1498.

Riggs, Jack E., et al., "Spastic Quadriparesis, Dysarthria, and Dysphagia following Cervical Hyperextension: A Traumatic Pontomedullary Syndrome", Military Medicine, 1995. 160(2): 94-95.

Rodier, Patricia M., "Converging evidence for brain stem injury on autism", Develop and Psychopath, 2002. 14: 537-557.

Rutter, Michael, et al., "Genetics and Child Psychiatry: II Empirical Research Findings", J Child Psychol Psychiatry, 1999. 40(1): 19-55.

Scahill, Lawrence, et al., "Children's Yale-Brown Obsessive Compulsive Scale: Reliability and Validity", J Am Acad Child Adol Psychiatry, 1997. 36(6): 844-852.

Scoville, W. B., et al., "The Cervical Ruptured Disc; Report of 115 Operative Cases", Trans Am Neurol Assoc, 1951. 56: 222-224.

Schneider, Richard C., et al., "The Syndrome of Acute Central Cervical Spinal Cord Injury", J Neurol Neurosurg Psychiatry, 1958. 21: 216-227.

Shuman, Sheri L., et al., "Apoptosis of Microglia and Ogliodendrocytes After Spinal Cord Contusion in Rats", J Neurosci Research, 1997. 50: 798-808.

Smith, C. G., "Changes in Length and Position of the Segments of the Spinal Cord with Changes in Posture in the Monkey", Radiology, 1956. 66(2): 259-265.

Stein, Mark A., et al., "Psychometric Properties of the Children's Atypical Development Scale", J Abnorm Child Psych, 1994. 22(2): 167-176.

Szatmari, Peter, "The Classification of Autism, Asperger's Syndrome, and Persuasive Developmental Disorder", Can J Psychiatry, 2000. 45(8): 731-738.

Szatmari, Peter, "The causes of autism spectrum disorders", BMJ, 2003. 326: 173-174.

Tachibana, Shigekuni, et al., "Spinal Cord Intramedullary Pressure. A Possible Factor in Syrinx Growth", Spine, 1994. 19(19): 2174-2179.

Tunturi, Archie R., "Elasticity of the spinal cord, pia, and denticulate ligament in the dog", J Neurosurg, 1978. 48: 975-979.

Wakefield, A J, et al., "Ileal-lymphoid-nodular hyperplasia, non-specific colitis, and pervasive developmental disorder in children", The Lancet, 1998. 351: 637-641.

Wing, Lorna, "Chapter 7—The Continuum of Autistic Characteristics", Diagnosis and Assessment in Autism, 1993. 91-110.

Wolf, John A., et al., "Traumatic Axonal Injury Induces Calcium Influx Modulated by Tetrodotoxin-Sensitive Sodium Channels", J Neurosci, 2001. 21(6): 1923-1930.

Zeegers, Mijke, et al., "Radiological findings in autistic and developmentally delayed children", Brain & Develop, 2006. 28: 495-499.

Povlishock, John T., "Traumatically Induced Axonal Injury: Pathogenesis and Pathobiological Implications", Brain Pathology, 1992. 2(1): 1-12.

Grob, D., et al., "Posterior Occipitocervical Fusion A Preliminary Report of a New Technique," Spine, vol. 16, No. 3 Supplement, Jan. 1, 1991, pp. S17-S24.

Sandhu, Faheem A., MD, PhD, et al., "Occipitocervical Fusion for Rheumatoid Arthritis Using the Inside-Outside Stabilzation Technique," SPINE, 2003, pp. 414-419, vol. 28, No. 4.

Kumar, Raj et al., "Management of Pediatric Congenital Atlantoaxial Dislocation: A Report of 23 Cases from Northern India," Pediatric Neurosurgery, 2002, pp. 197-208, vol. 36.

Co-Pending U.S. Appl. No. 12/638,930, filed Dec. 15, 2009.

Co-Pending U.S. Appl. No. 12/688,848, filed Jan. 15, 2010.

International Search Report and Written Opinion for International Application No. PCT/US2011/021351 Dated Sep. 21, 2011.

* cited by examiner

FIG. 21
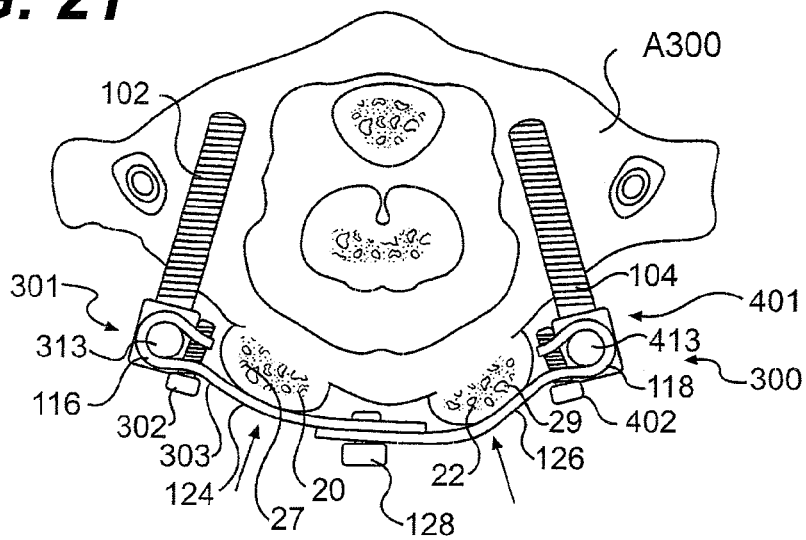
FIG. 22
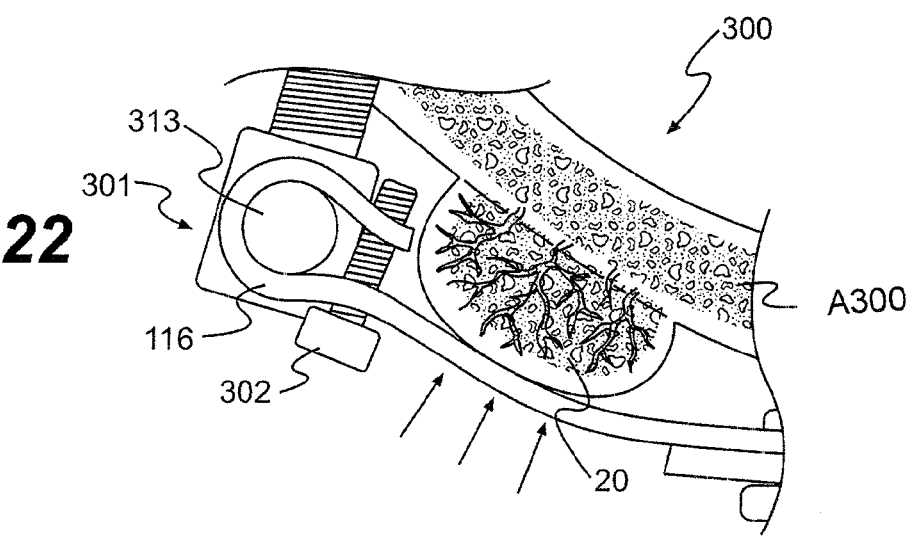
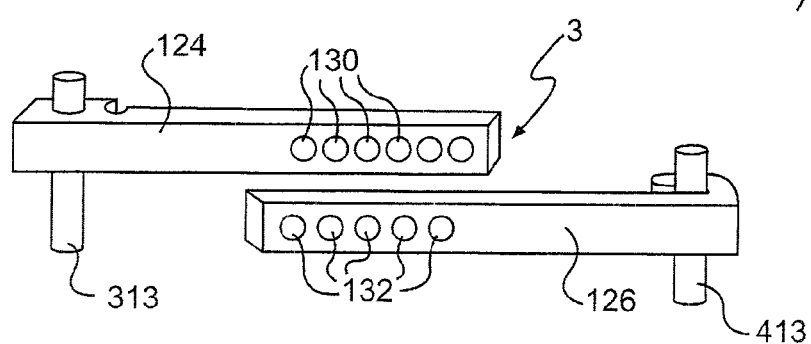
FIG. 23

VERTEBRA ATTACHMENT METHOD AND SYSTEM

CROSS-REFERENCE TO RELATED APPLICATIONS

This application is a continuation in part of U.S. patent application Ser. No. 11/832,643, filed on Aug. 1, 2007, which in turn claims the benefit of U.S. Provisional Patent Application No. 60/887,022, filed on Jan. 29, 2007; continuation in part of U.S. patent application Ser. No. 11/832,646, filed on Aug. 1, 2007, which in turn claims the benefit of U.S. Provisional Patent Application No. 60/887,022, filed on Jan. 29, 2007; and further benefit of U.S. Provisional Patent Application No. 60/987,567, filed Nov. 13, 2007; the entire disclosures of which are incorporated herein by reference.

BACKGROUND OF THE INVENTION

1. Field of Invention

The present invention is directed to a novel vertebra attachment method and system. Specifically, the invention pertains to a vertebra attachment method and system that may be used in spinal stabilization applications, such as fusing the occipitocervical junction and/or the spinal vertebrae.

2. Brief Description of the Prior Art

I. Spinal Anatomy

As shown in FIG. 1, the human spinal column A100 is comprised of a plurality of vertebrae A1 which are divided into five regions. The cervical region includes seven vertebrae, C1-C7. The thoracic region includes twelve vertebrae, T1-T12. The lumbar region contains five vertebrae, L1-L5. The sacral region is comprised of five vertebrae, S1-S5, and the coccygeal region contains four vertebrae, Co1-Co4.

The C1 vertebra A200 is the first vertebra of the spinal column and has a unique structure that enables it to support cranium A500. C1 vertebra A200 functions as a "sesamoid bone" between the C2 vertebra A300 and the cranium A500, enabling 45° left and right rotation and approximately 20° of flexion and extension. It is the most mobile bone in the body and allows for an extraordinary degree of repetitive movement with four degrees of freedom.

As shown in FIG. 2, the C1 vertebra A200 has an anterior arch A2, a posterior arch A3 and two lateral masses A4. The posterior arch A4 comprises ⅖ths of the circumference of the vertebra and terminates at the dorsal midline in the posterior tubercle A5 and at the rudimentary spinous process A6, The space between the lateral masses A4 is primarily occupied by the odontoid process A7, which is held in place by the transverse odontoid ligament A8.

Unlike the other vertebrae of the spinal column, the vertebral body of the C1 vertebra, i.e. odontoid process A7, remains separated from the remainder of the C1 vertebra A200; odontoid process A7 also embryologically forms part of the C2 vertebra A300. The C2 vertebra A300 therefore enables rotation of the C1 vertebra A200 around the odontoid process A7.

The C1 vertebra A200 also includes a pair of transverse foramina A10, located on the upper surface of the posterior arch A2 on either side of the spinal cord A11. Transverse foramina A9 directs vertebral artery A12 from lateral mass A4 to the upper surface of the posterior arch A3, where it continues into cranium A500, and supplies blood to the brainstem and occipital lobes of the brain. The vertebral artery is supported by a groove of the transverse foramina A9 on the surface of the posterior arch of the C1 vertebra A200 which may vary in size and depth. This groove can be bridged by anomalous ossification and posterior ponticulus.

The grooves A10 in the posterior arch A3, along which passes the first cervical nerves and vertebral arteries A12 from a lateral to a medial position are known as the transverse foramina A9; the foramina A9 generally guide the vertebral arteries A12 through lateral masses A4.

Lateral masses A4 are the most bulky parts of the C1 vertebra A200 and constitute the primary weight bearing surface for supporting cranium A500. Lateral masses A4 are ovoid and provide articular surfaces for the occipital condyles above, located at the base of the skull, and the lateral masses of the C2 vertebra A300 below. Due to their substantial bulk and load bearing capability, lateral masses A4 are typically selected as the location for screw placement during spinal fixation.

In contrast to the specialized anatomy of C1 vertebra A200, the anatomy of a more standard vertebra is illustrated in FIG. 3's depiction of the lumbar vertebra A400. Although the location of the physiological components of the lumbar vertebrae A400 may vary, its anatomy is similar to most vertebrae.

In general, most vertebrae include a vertebral body A13. Two short bones, the pedicles A14, extend backward from each side of the vertebral body A13 to form a vertebral arch A15. At the posterior end of each pedicle A14, vertebral arch A15 flares out into broad plates of bone, known as laminae A16. Laminae A16 fuse with each other to form a spinous process A17, which enables muscle and ligamentous attachment. A smooth transition from the pedicles A14 into laminae A16 is interrupted by the formation of a series of processes. Two transverse processes A18 thrust out laterally on each side from the junction of pedicle A14 with lamina A16. These transverse processes A18 serve as levers for the attachment of muscles to the vertebrae. Four articular processes, two superior A19 and two inferior A20, also arise from the junctions of pedicles A14 and laminae A16. The superior and inferior articular processes A19 and A20 each have a natural bony structure known as a facet; superior articular facet A21 faces dorsally, slightly and upward (cranially), while inferior articular facet A22 faces ventrally and downward (caudally).

As shown in FIG. 4, when adjacent vertebrae are aligned, facets A21 and A22, capped with a smooth articular cartilage, interlock to form a facet joint A23, also known as a zygapophysial joint. An intervertebral disc A24 positioned between each pair of vertebrae permits a small amount of cushioned movement between the vertebrae. Thus, the structure and alignment of the vertebrae permit movement of the vertebrae relative to each other.

II. Spinal Stabilization Methods

Spinal instability is a severe problem, and may cause chronic, subacute or acute compression of the upper spinal cord. Instability of the uppermost vertebrae, C1 and C2, may result in compression of the medulla oblongata, and may cause significant neurological problems, such as altered sensation and motor function, altered respiratory function, altered cardiac, gastrointestinal, bowel and bladder function, or altered function of the autonomic nervous system. Compression may also cause neck pain, headache and bulbar symptoms, such as altered vision and hearing, difficulties with swallowing, altered speech, sleep apnea, numbness and weakness of the arms and legs, urinary urgency or incontinence, or the progressive loss of ability to walk. Sudden death may even occur upon the sudden compression of the medulla or upper spinal cord.

Conventional surgical methods for spinal stabilization, specifically stabilization of the occipitocervical junction, to correct injuries due to trauma or chronic spinal conditions, such as degenerative, metabolic, congenital, endocrinological, neoplastic or infectious spinal diseases are well known. Current stabilization techniques typically involve fixation of at least the C1 and C2 vertebrae A200, A300 to the cranium A500. Examples of conventional stabilization methods include posterior internal fixation involving procedures, such as the Brooks and Gallie technique, Magerl's transarticular screw technique, and the Harms and Melcher polyaxial screw fixation techniques.

A particularly effective conventional method for rigid fixation of the occipitocervical fixation involves inserting a screw under the transverse foramina A10 into the lateral mass A4 of the C1 vertebra A200. Additionally, insertion of C2 pedicle screws is also a frequently practiced technique for occipito-atlanto-axial fixation. In general, screw fixation has thus far been limited to insertion within the lateral mass A4 and pedicles A14. Although proven to have superior biomechanical capabilities and fusion rates in comparison to wiring techniques, screw fixation is a demanding technique and carries a substantial risk of injuring vertebral artery A12. The method can be highly dangerous, potentially severing or causing substantial harm to the vertebral artery A12, shown in FIG. 6.

Blockage or thrombosis of the vertebral artery A12 can result in immediate brainstem stroke, "locked-in syndrome," or death. Conventional spinal stabilization methods, which requires inserting screws in the C1 lateral mass A4, risks injuring the artery A12 at three locations: below the vertebral artery foramen A9, within the vertebral artery foramen A9 of the lateral mass A4, and in the transverse foramen A10, These injuries to the vertebral artery A12 arise for three reasons; first, an errant screw may be inserted incorrectly and project below the vertebral artery foramen A9 striking the artery A12 before it enters the vertebral artery foramen A9; second, when the vertebral artery foramen A9 lies more medial than usual, which commonly occurs in 20-30% of patients, placement of the C1 lateral mass screw with the standard technique impales the aberrant vertebral artery A12; third, the presence of a bone anomaly in which the vertebral artery A12 is hidden by a bone bridge over the transverse foramen A10, i.e. Kimmerle's anomaly also known as the "arcuate foramen" which has an 1.14% to 18% occurrence rate, precludes the safe identification and exposure of the artery A12 and may also result in the artery A12 bulging outward in areas where it is not covered by the bone abnormality.

The vertebral artery A12 may also be injured during the surgical exposure of the operative site. The vertebral artery A12 may derive from the internal carotid artery and enter into the space between the occiput and C1 vertebra arch, i.e. Pro-atlantal artery variant Type 1, or derive from the external carotid and enter between the C1 vertebral arch and C2 lamina, i.e. Pro-atlantal artery variant Type 2. In each case, the vertebral artery A12 in its anomalous course is at an increased risk of injury. Moreover, dissection of the lateral aspect of the lateral mass of C1 may result in injury and tearing of the vertebral artery A12 because: artery A12 frequently sits in an exposed position above rather than within the groove; there is a risk of avulsion of several vessels arising from the vertebral artery A12 and the muscular branch of the vertebral artery; and anomalous variants or rotation of the C1 vertebra places the vertebral artery A12 in the path of surgical exposure.

Moreover, wide exposure of C1 vertebra required by conventional lateral mass screws fixation techniques may injure collateral blood supply. The occipital artery, through which vertebral artery A12 may receive its blood supply may be injured or compressed during exposure of the surgical site. Injury to these collateral arteries may consequently decrease blood supply to the vertebral artery A12, and may potentially cause a stroke.

The lateral mass screw may also injure the covering of the spinal cord, known as the dura. A screw placed too close to the midline, may thus induce a cerebrospinal fluid leak. The C1 screw may also cause severe headaches by damaging the C2 nerve root A23, which exits just medial to where the C1 screw should be placed. Additionally, if the C1 screw is inserted too deep and passes into the retropharynx, it may cause hematoma or pass into the pharyngeal cavity, thereby introducing bacteria into the retropharyngeal space or C1 anterior arch, and cause a serious infection. Therefore, screw placement on the C1 lateral mass carries significant risk.

Furthermore, conventional atlantoaxial transarticular screw fixation techniques may be inapplicable in several instances. It may be impossible to place a screw into a lateral C1 mass that is congenitally diminutive or eroded by trauma, neoplasm, or other pathological processes. Irreducible C1 and C2 subluxation may further preclude optimum placement of atlantoaxial transarticular screws, since the correct screw trajectory traversing the articular surfaces of C1 and C2 cannot be achieved. Severe cervicothoracic kyphosis may contraindicate C1 and C2 transarticular screw placement by obstructing the trajectory of the instruments used to insert the screws. Therefore, in addition to being dangerous, conventional lateral mass screw fixation may not be possible.

Despite the inherent difficulties and extreme danger of placing screws in the lateral mass of the C1 vertebra and similar risks involved in screw fixation of other vertebra, these lateral mass screw fixation procedures are becoming more commonplace. Therefore, there is a need to develop a vertebral attachment method that is safe and effective as well as a system that minimizes or eliminates injury to vertebral artery A12 and spinal cord A11.

SUMMARY OF THE INVENTION

Accordingly, it is an object of the invention to provide a method and system that accomplishes the goals of: successfully minimizing or eliminating the risk of severing, compressing, impinging or otherwise injuring the vertebral artery, vertebral vein, spinal nerve roots and/or spinal cord; developing a vertebral attachment system that may assist in the stabilization of the occipitocervical junction or the junctions between lower vertebrae; and minimizing the necessary duration of the surgical procedure. In order to achieve the above and other objects of the invention, the present invention is directed to a novel vertebral attachment method and system.

In a first aspect, the invention may be directed to an attachment system including a clamp that at least partially surrounds a posterior region of a vertebra, wherein the clamp has a first member, a second member, and an aperture. The system further includes a plate having an aperture, and a fastener, wherein the fastener extending through said apertures to secure the plate and clamp to the posterior region.

In a second aspect, the invention is directed to an attachment system including a clamp that at least partially surrounds the posterior arch of the C1 vertebra, wherein the clamp has a first member and a second member, each of which has an aperture. The system further includes a plate having an aperture, and a fastener, wherein the fastener extending through said apertures to secure the plate and clamp to the posterior region.

In a third aspect, the invention is directed to an attachment method that involves providing an attachment system, placing a clamp on the posterior region of a vertebra, aligning the first, second and third apertures, and fastening the attachment system to the vertebra by inserting the fastener thorough the first and second apertures.

BRIEF DESCRIPTION OF THE DRAWINGS

FIG. 21 is a cross-sectional view depicting certain components of the system that is shown in FIG. 16;

FIG. 22 is a cross-sectional view depicting certain components of the portion of the system shown FIG. 14 that is depicted in FIG. 21;
FIG. 23 is a side view of an exemplary embodiment of a plate.

DETAILED DESCRIPTION OF THE PREFERRED EMBODIMENTS

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Thus, for example, reference to "clamp" may include a plurality of clamps and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The present invention is directed to novel vertebra attachment systems and vertebral fastening methods. The technological basis of the invention is predicated upon the importance of developing an effective vertebral attachment system and method that may accomplish the following: first, enable spinal stabilization; second, prevent severing, compressing, impinging or otherwise injuring critical structures, such as the vertebral artery, vertebral vein, spinal cord, nerve roots exiting the spinal cord or a combination thereof during implant; and third, minimize the overall surgical duration. This may be accomplished by positioning a uniquely configured attachment system on a posterior region of a vertebra, distal from the aforementioned critical structures of the spine.

I. System

Figure 1:
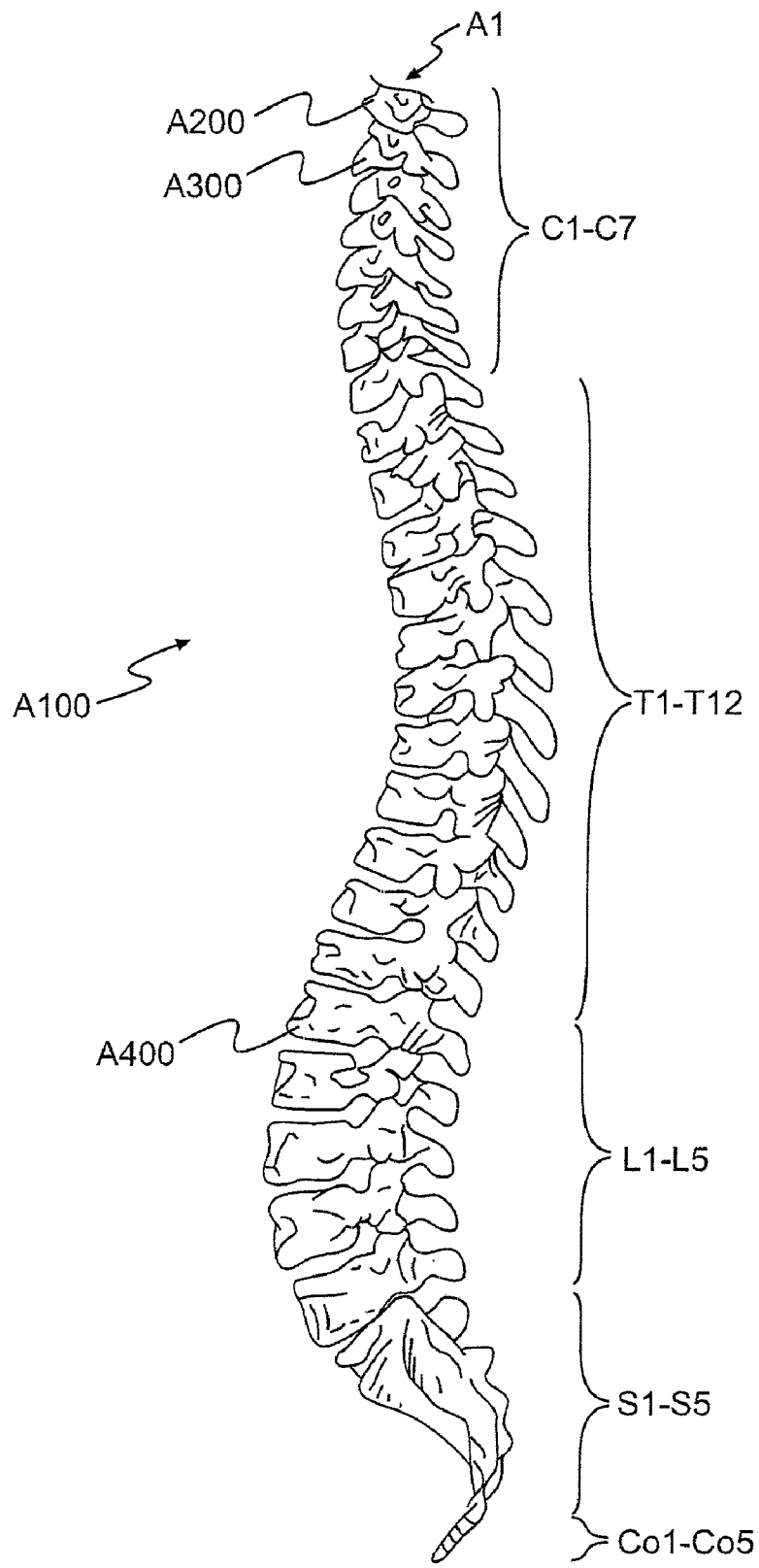
FIG. 1 is a perspective view of a human spinal column.
Figure 2:
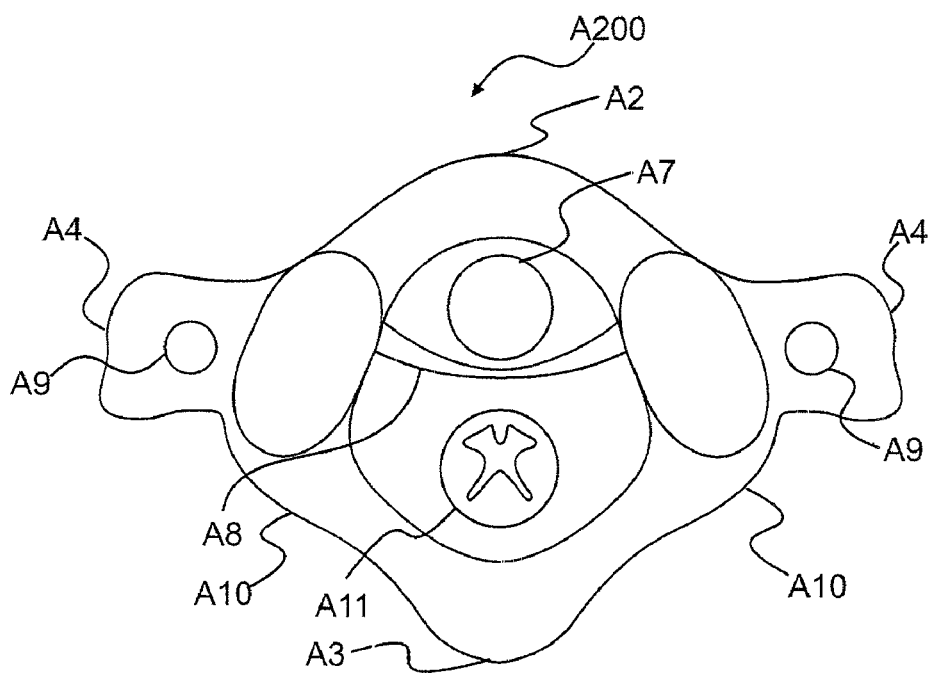
FIG. 2 is a cross sectional view of a C1 vertebra.
Figure 3:
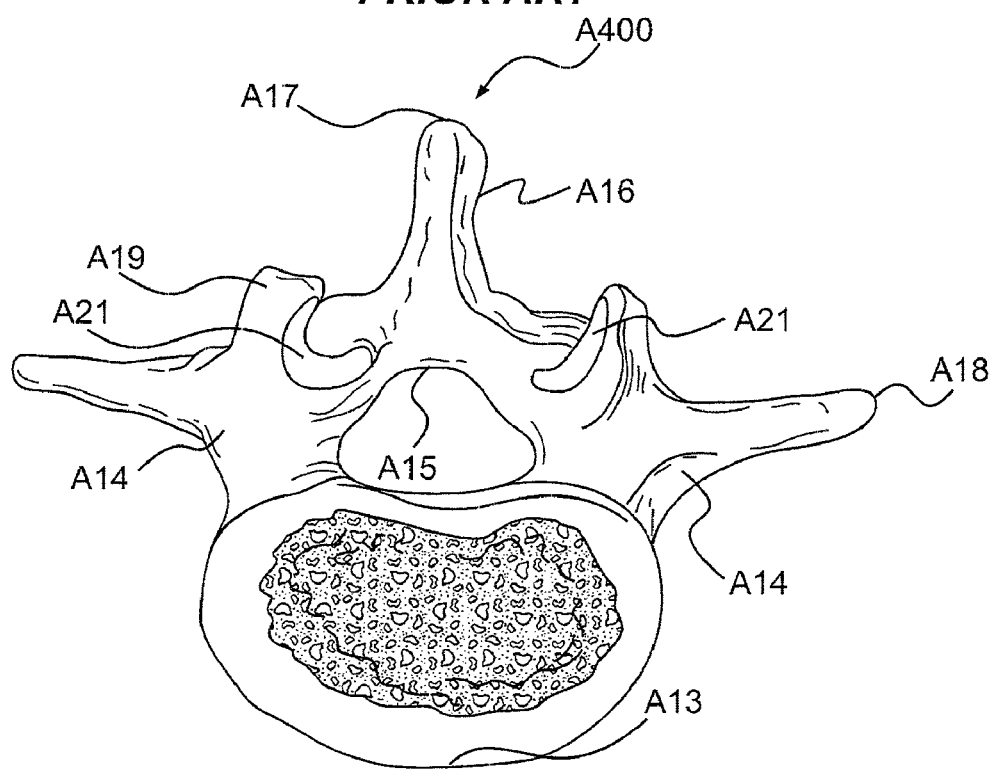
FIG. 3 is a perspective view of a lumbar vertebra.
Figure 4:
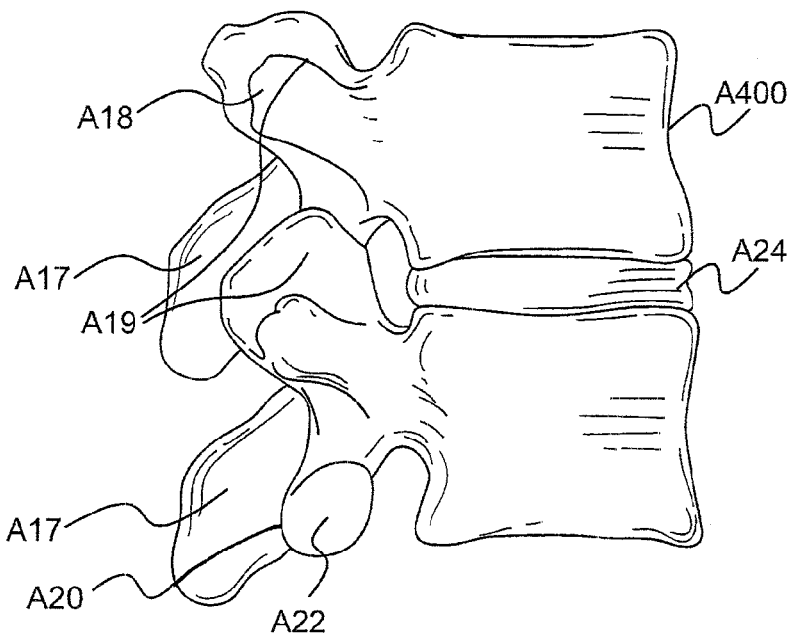
FIG. 4 is a perspective view of a vertebral lumbar facet joint.
Figure 5:
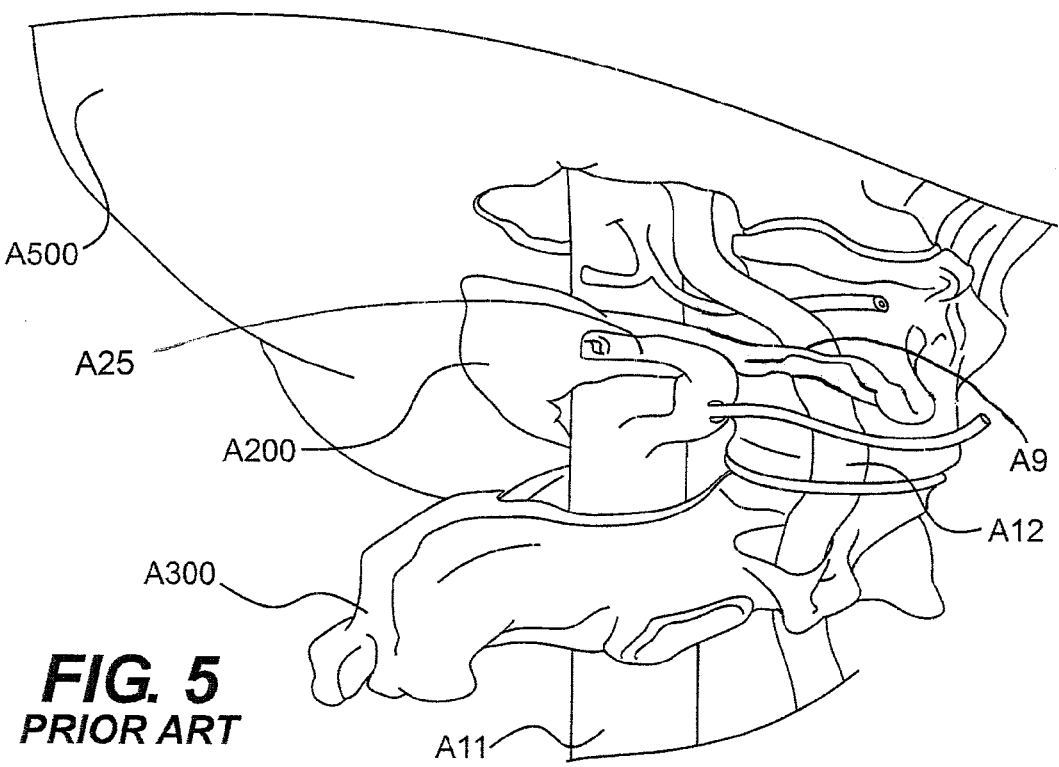
FIG. 5 is a perspective view of the vertebral artery and C1 nerve relative to the C1 vertebra.
Figure 6:
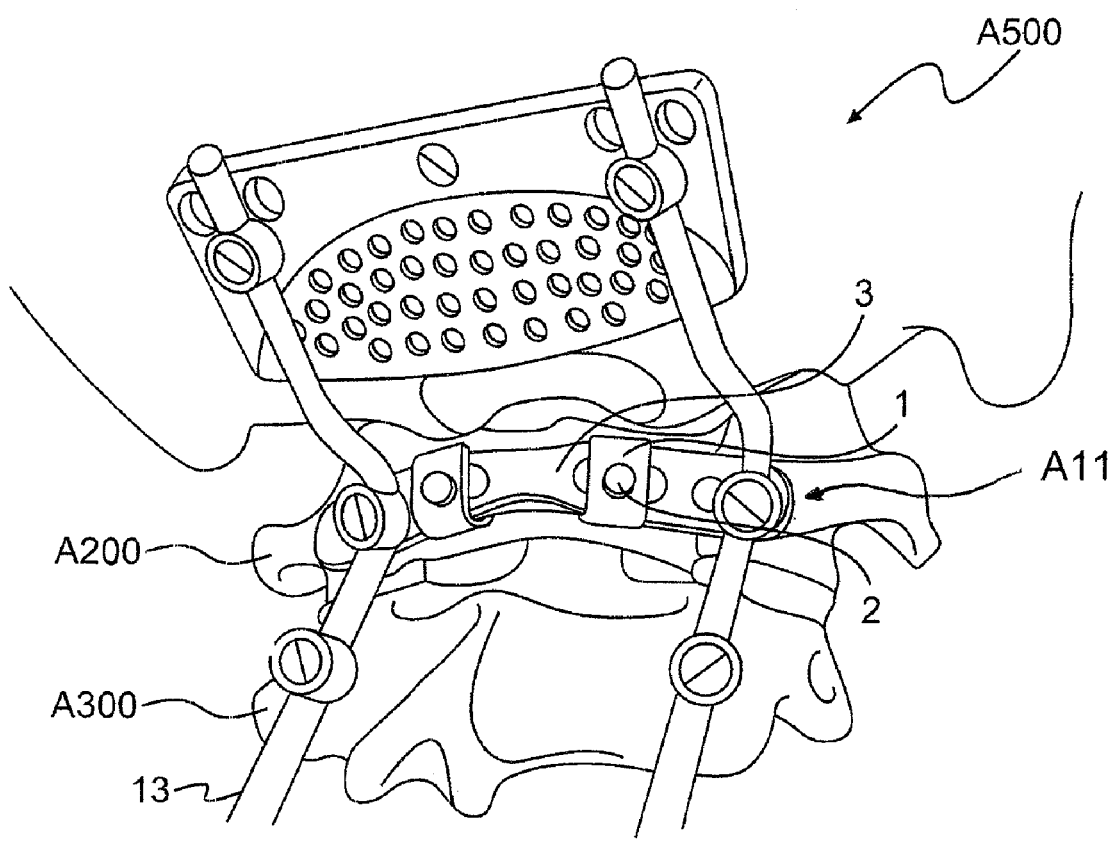
FIG. 6 is a perspective view of an exemplary embodiment of a C1 attachment system being utilized to connect the C1 vertebra to another system that stabilizes the skull and spine.

In accordance with an exemplary embodiment of the invention, FIG. 6 shows an attachment system 100 that includes at least one clamp 1, at least one fastener 2, and at least one vertebral plate 3 configured to be securely fastened to any vertebra A1 of the spinal column A100. Attachment system 100 is designed such that clamp 1 and fastener 2 securely anchor vertebral plate 3 to a portion of vertebra A1. Vertebral plate 3 in turn may be connected to other orthopedic structures and assemblies. In an exemplary embodiment, attachment system 100 may be structurally configured to enable attachment to a posterior region of vertebra A1 and may be able to withstand at least normal spinal loads. It is envisioned that the system of the present invention may be compatible with any orthopedic structure or assembly to enable spinal stabilization between vertebrae and/or enable stabilization of the occipitocervical junction.

Figure 7A:
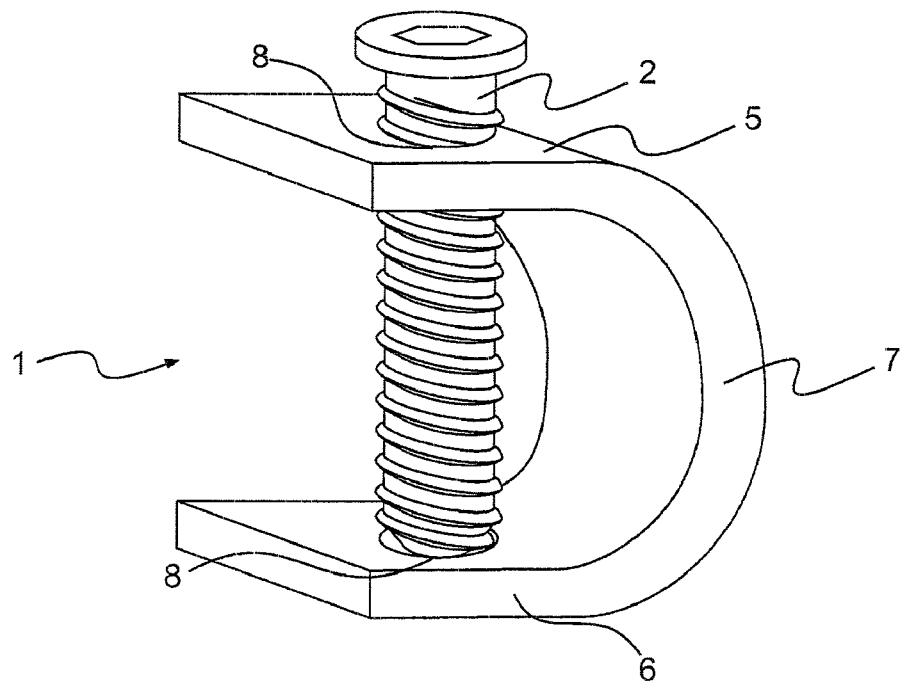
FIG. 7(a) is a perspective view of an exemplary embodiment of the clamp.
Figure 7B:
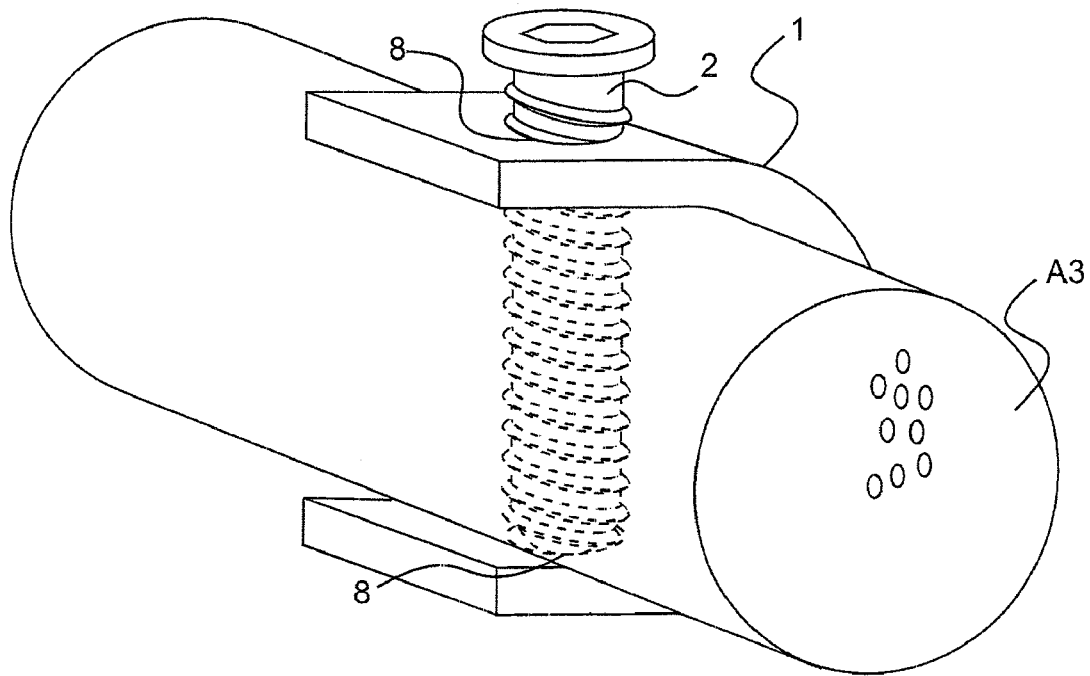
FIG. 7(b) is a perspective view of an exemplary embodiment of the clamp on the posterior region arch of the C1 vertebra.

Clamp 1 may be any device capable of at least partially or wholly surrounding a portion of vertebra A1, and clamp 1 may have any dimension, configuration or geometric shape suitable for gripping, clasping, clipping or otherwise retaining a portion of vertebra A1. In an exemplary embodiment, at least one portion of clamp 1 conforms to a surface of vertebra A1. As shown in FIGS. 7(a)-7(b), clamp 1 may include a curved surface having a circumference of approximately 4 radians that encircles a portion of posterior arch A3 of the C1 vertebra A200. Preferably, clamp 1 may be sized and shaped to surround a posterior region of vertebra A1. In an exemplary embodiment, clamp 1 may have at least two members 5, 6 separated by a space sized to accommodate a portion of vertebra A1. Clamp 1 may also include at least one other member 7 to further facilitate the retention of vertebra A1. As shown in FIG. 7(a), clamp 1 may have a U, semi-circular or collar like shape. Preferably, clamp 1 is configured to be sufficiently thin and have a low profile such that it does not substantially obstruct, compress or impinge any adjacent vertebral components.

In an exemplary embodiment, at least one aperture 8 may be located on clamp 1 for receiving fastener 2. The inner surface of aperture 8 may be smooth, partially threaded or completely threaded; aperture 8 may also include bevels, collars, insets or any other structure that would facilitate the retention of fastener 2. In an exemplary embodiment, clamp 1 may include a plurality or at least one pair of apertures 8. Preferably, at least one aperture 8 may be located on a first member 5 and on a second member 6 of clamp 1 such that said apertures are geometrically aligned. Apertures 8 of clamp 1 may have a variety of different sizes and shapes to accommodate different fasteners 2.

Clamp 1 may be fabricated from any high strength and biocompatible material. In an exemplary embodiment, clamp 1 may be fabricated from any material having sufficient material and mechanical properties that would enable load bearing applications including spinal stabilization. The material used to fabricate clamp 1 may include a biocompatible metal, metal alloy, ceramic, polymer, such as a polymer from the polyaryletherketone family (PAEK) family, such as polyether ether ketone (PEEK) or polyether ketone ketone (PEKK), or composite material. Preferably, the material may include a metal alloy, such as titanium. Optionally, the surface of clamp 1 may be treated to adjust the frictional, wear or biocompatibility properties of clamp 1. In an exemplary embodiment, at least one portion of clamp 1 may be coated with a material, contoured, and/or textured to limit a range of motion of clamp 1 relative to the vertebra A1 and/or vertebral plate 3. In another embodiment, clamp 1 may be coated with a material to minimize wear of clamp 1 and/or facilitate osteointegration.

Attachment system 100 may include any number of clamps 1 to attach vertebral plate 3 to vertebra A1. In an exemplary embodiment, a sufficient number of clamps 1 may be attached to vertebra A1 to enable spinal stabilization applications. Preferably, the system may include at least about one to three clamps 1, more preferably, about two to three clamps 1.

As shown in FIGS. 7(a)-7(d), fastener 2 may removably secure clamp 1 to vertebra A1. Fastener 2 may be any element that is compatible with clamp 1 and vertebral plate 3 so as to enable load bearing applications, such as spinal stabilization. Fastener 2 may have any suitable dimension, configuration or geometric shape. In an exemplary embodiment, fastener 2 may include a threaded component, hook, latch, pin, nail, wire, tether, or combinations thereof. Preferably, fastener 2 may be sized and shaped to secure clamp 1 to a posterior region of vertebra A1. Attachment system 100 may include a plurality of fasteners 2 having different configurations and/or dimensions compatible with clamp 1 and vertebral plate 3.

Fastener 2 may be fabricated from any material suitable for securing clamp 1 to vertebra A1. In an exemplary embodiment, fastener 2 may be fabricated from any high strength and biocompatible material. The material used to fabricate fastener 2 may include a biocompatible metal, metal alloy, ceramic, polymer, such as a polymer from the polyaryl ether ketone family (PAEK) family, such as polyether ether ketone (PEEK) or polyether ketone ketone (PEKK), or composite material. Preferably, the material may include a metal alloy, such as titanium.

Optionally, fastener 2 may also include a lock 9 to further secure the retention of a portion of vertebra A1. Lock 9 may be any mechanism that ensures that fastener 2 is securely attached to clamp 1, vertebral plate 3 and/or vertebra A1. Lock 9 may also have any suitable dimension, configuration or geometric shape and may be fabricated from any suitable material. In an exemplary embodiment, lock 9 may be a threaded component, hook, latch, pin, nail, wire, tether, or combinations thereof.

Figure 8:
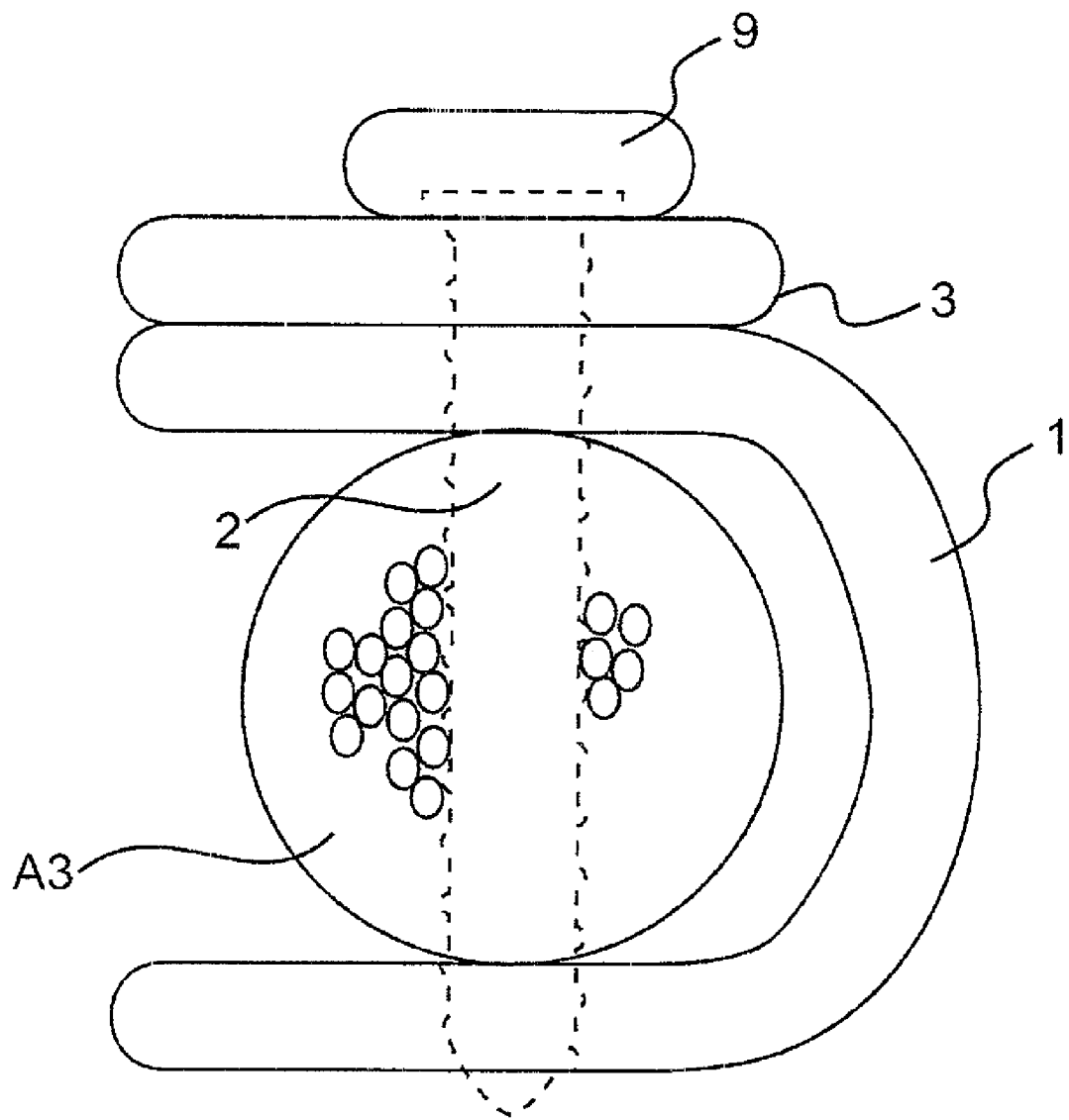
FIG. 8 is a cross section of a screw placed through the plate, the clamp, and posterior arch of the C1 vertebra that is secured with a spiral locking mechanism in the screw head.

In an exemplary embodiment, lock 9 may be threaded component, such as a screw, bolt, rivet, or nut. As shown in FIG. 8, lock 9 may be a nut coupled to the head of fastener 2. Fastener 2 may be secured by preventing it from being unscrewed or otherwise detached from clamp 1, vertebral plate 3 and/or vertebra A1 without first removing the nut. In one example, to remove the nut, it must be turned in the opposite direction in which a threaded fastener 2 must be turned to detach fastener 2.

Figure 7C:
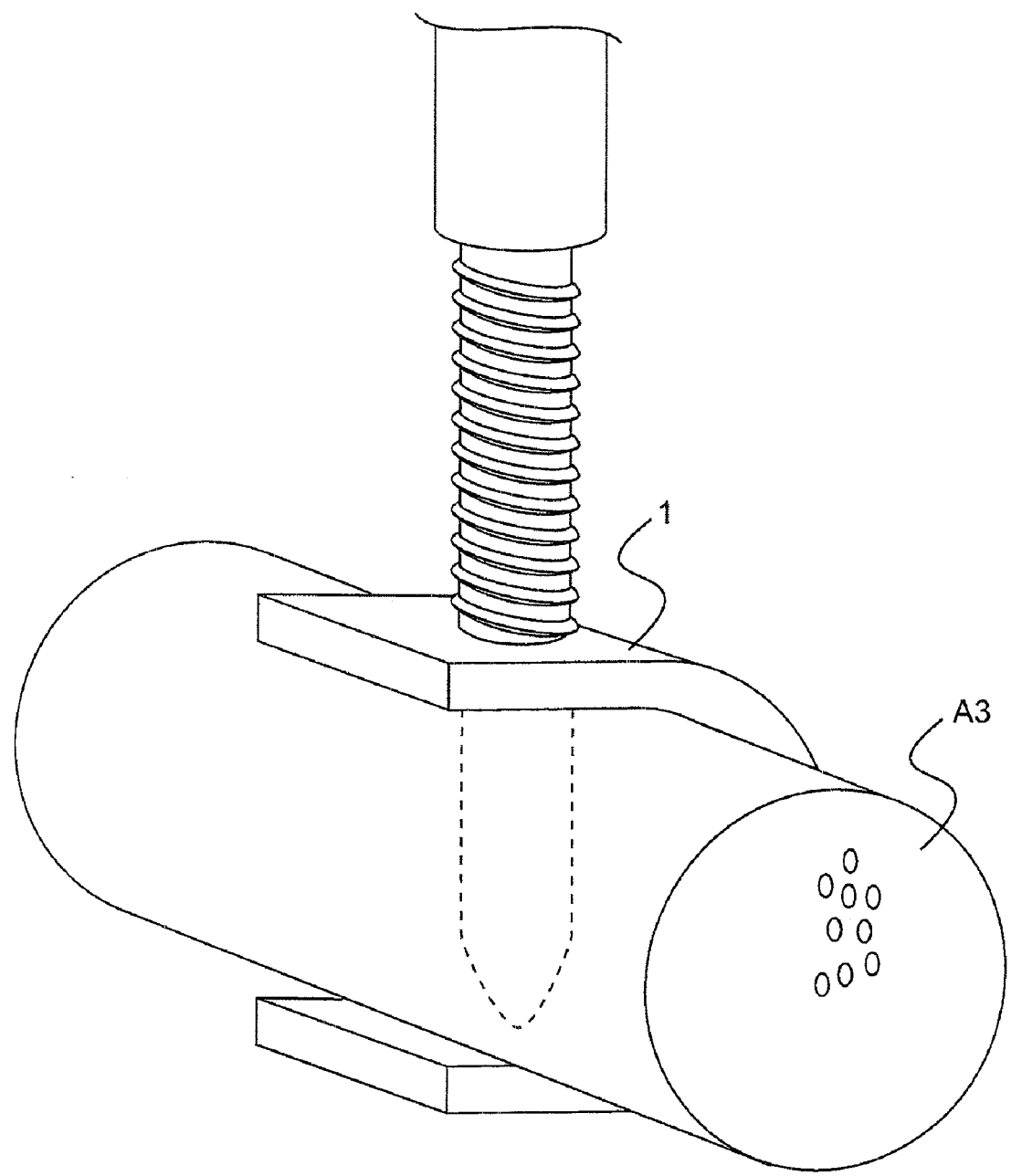
FIG. 7(c) shows a drill creating a hole that penetrates the posterior arch of the C1 vertebra from the dorsal to ventral side.

As shown in FIGS. 7(a)-7(c), in one exemplary embodiment, fastener 2 may be a threaded component, such as a screw, rivet, or bolt. Preferably, fastener 2 may be a triple screw which possesses three functional portions along the length of the screw: a threaded portion for attachment to bone; a threaded or non-threaded portion to engage vertebral plate 3, and a threaded or non-threaded portion to engage clamp 1. The triple screw may provide increased stability by virtue of the combined fixation of the screw within vertebral plate 3, clamp 1 and the vertebra A1. The threaded component may have a small diameter, for example, about 1.5 mm to about 4 mm and a length of about 6 to about 20 mm. Fastener 2 may couple clamp 1 to vertebra A1 by penetrating a portion of vertebra A1 and clamp 1 at the dorsal and/or ventral apertures 8. Fastener 2 may also include a lock 9, such as a nut, that prevents loosening under applied physiological loads. In the exemplary embodiment shown in FIG. 7(a), the tip of fastener 2 does not extend substantially past ventral aperture 8 of clamp 1 so as to injure the vertebral artery A12, vertebral vein, spinal nerve roots and/or spinal cord.

Figure 7D:
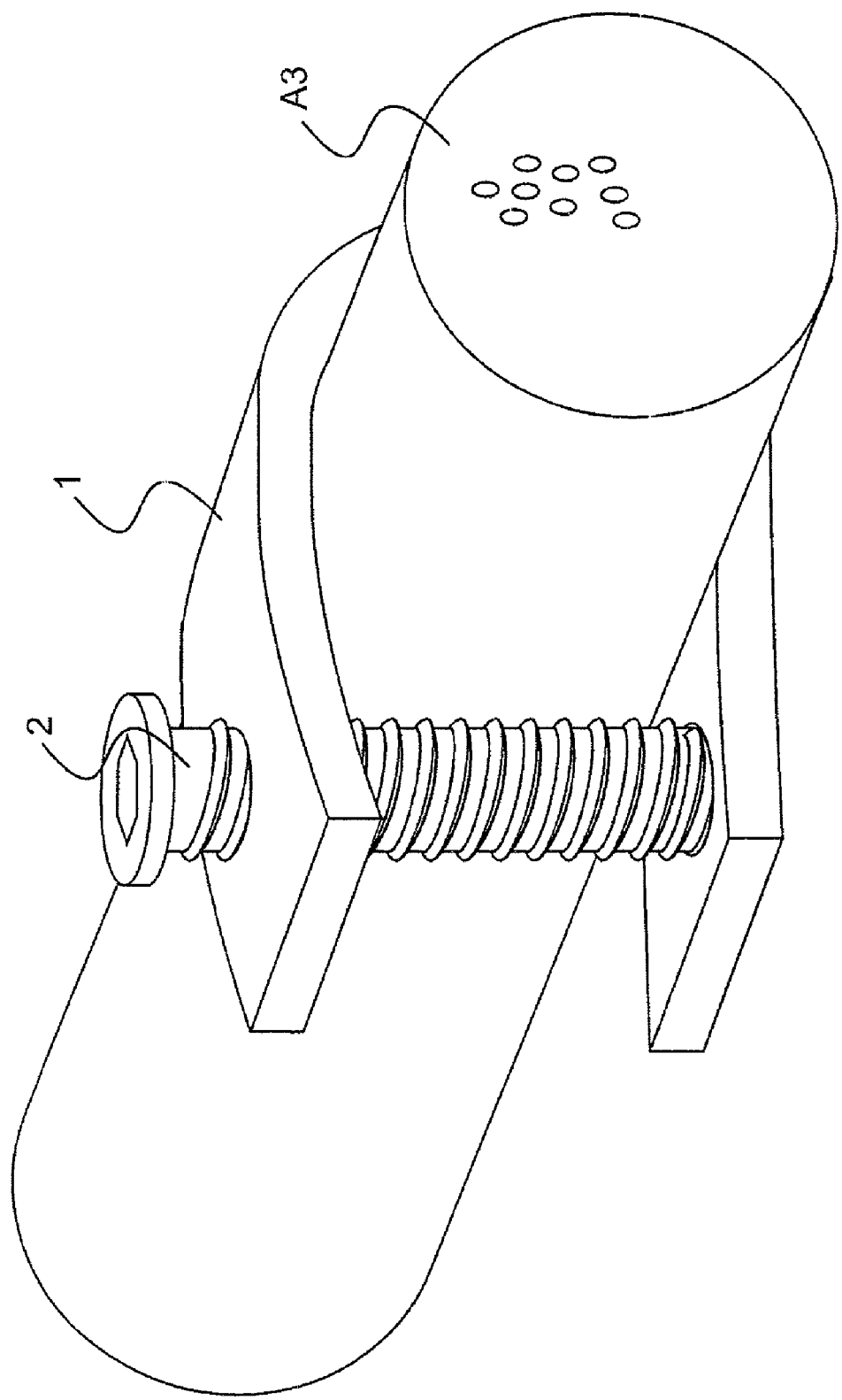
FIG. 7(d) is a perspective view of a screw placed through the clamp and adjacent to the posterior arch of the C1 vertebra.

In the alternative exemplary embodiment of FIG. 7(d), fastener 2 may be located adjacent to but does not penetrate the vertebra. In this embodiment, fastener 2 extends through clamp 1 at the dorsal and/or ventral apertures 8, and secures vertebra A1 by functioning as a clasp or latch, passing adjacent to the vertebra. Because fastener 2 does not penetrate the vertebral body, this embodiment minimizes trauma and vertebra erosion. When fastener 2 is a triple screw, the length of the screw that extends adjacent to the vertebral body may optionally be non-threaded in this embodiment. As discussed above, fastener 2 may also include a lock 9 to prevent loosening under applied physiological loads.

Figure 9:
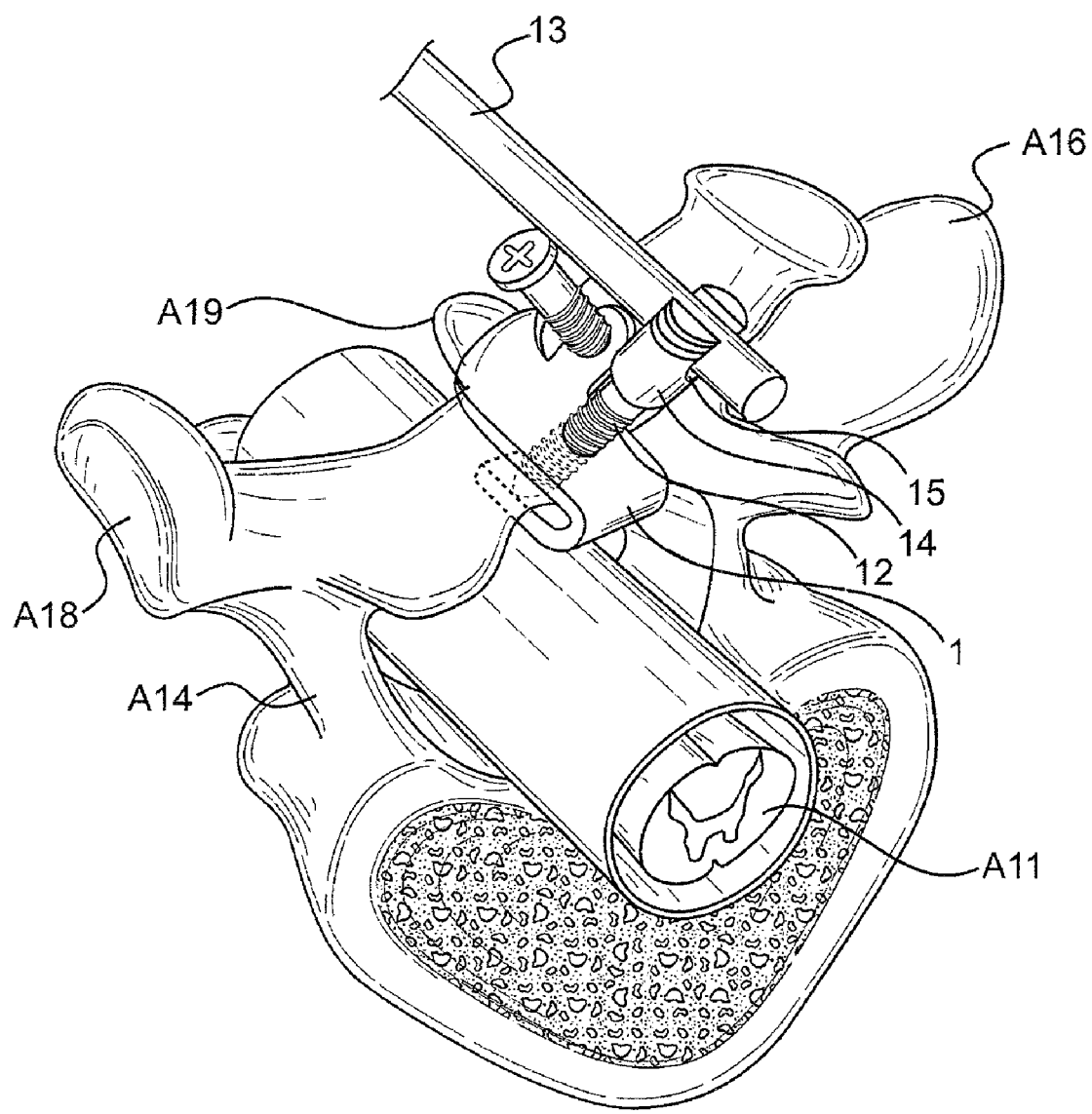
FIG. 9 is a perspective view of an exemplary attachment system wrapping around the spinous process of the thoracic vertebra using sublaminal screws.

Fastener 2 may be used to attach clamp 1 to any portion of vertebra A1 that would enable load bearing applications, such as spinal stabilization. In exemplary embodiment, clamp 1 and fastener 2 may be attached to a posterior region of vertebra A1, preferably at a location sufficiently distanced from the vertebral artery A12, vertebral vein, spinal nerve roots, spinal cord or a combination thereof to minimize the risk of possibly severing, compressing, impinging, or otherwise injuring the aforementioned spinal components. In an exemplary embodiment, clamp 1 and fastener 2 may be attached to the posterior arch A3 of the C1 vertebrae A200. Clamp 1 and fastener 2 may also be attached to a posterior region, such as the spinous process, pedicle or lamina, of the lumbar vertebrae, thoracic vertebrae, sacrum vertebrae, or coccygeal vertebrae. FIG. 9 shows attachment system 200 attached to a posterior region of an upper level thoracic vertebra, wherein a translamina screw engages the spinal canal by penetrating the cancellous and/or cortical bone of vertebra A1 to secure attachment system 200. The same attachment system 200, with minor modifications, may be similarly located on any cervical, thoracic or lumbar vertebrae.

Figure 10A:
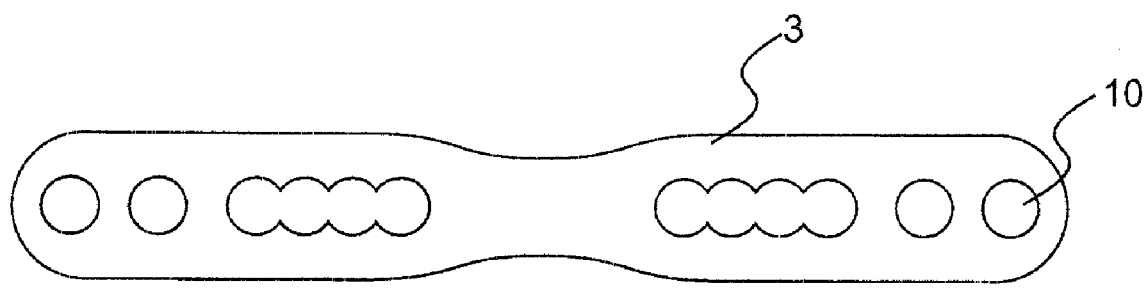
FIG. 10(a) is a top view of an exemplary embodiment of a plate.

As shown in FIG. 10(a), attachment system 100 of the present invention may further include at least one modular vertebral plate 3 that may be attached to clamp 1 and vertebra A1 using fastener 2. Vertebral plate 3 functions as a scaffold that may be fastened to and stabilize one more other orthopedic structure, including spinal stabilization assemblies. Vertebral plate 3 may optionally be used to also position and bias a bone graft material, such as bone, a bone substitute or other non-osseous material, into close contact with and/or under pressure against, at least one vertebra A1 so as to promote bone fusion.

Figure 10B:
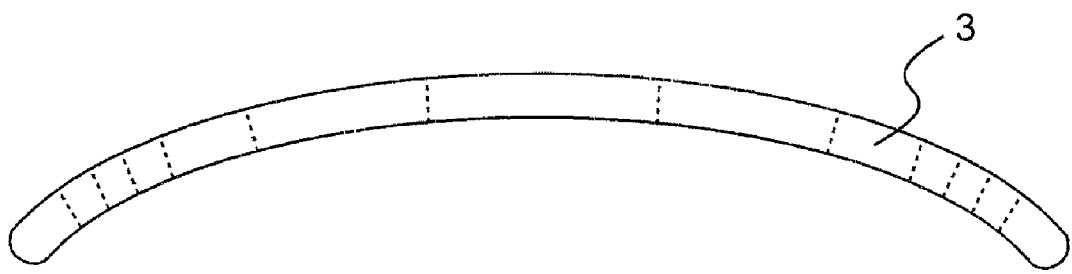
FIG. 10(b) is a side view of an exemplary embodiment of the plate shown in 9(a).

Vertebral plate 3 may have any configuration, shape or dimension that may be compatible with clamp 1 and fastener 2 and that may enable load bearing applications, such as spinal stabilization. In an exemplary embodiment, the system may include a plurality of vertebral plates having different dimensions, configurations and sizes that may be customized to different vertebral regions or application. As shown in the exemplary embodiment of FIG. 10(b), vertebral plate 3 may be curved along a portion of its body which may correspond to the curved surface of the C1 vertebra's A200 posterior arch A3. Preferably, vertebral plate 3 may be sized and/or shaped to complement a posterior region of vertebra A1. As shown in FIG. 6, vertebral plate 3 may be a thin curved plate having at least one dimension that is approximately the same as that of vertebra A1.

Vertebral plate 3 may also be elevated or extended to accommodate an enlarged vertebra caused by expansion duroplasty or an increased spinal canal size. In an exemplary embodiment, vertebral plate 3 may further include structure for adjusting a length of vertebral plate 3, whereby a lateral spacing distance between said first and second laterally spaced fastener 2 may be adjusted. In a preferred embodiment, this may be accomplished by constructing vertebral plate 3 out of two separate components that are attachable to each other, specifically a first connector portion 124 and a second connector portion 126, as is best shown in FIG. 22. The plurality of apertures 130, 132 in vertebral plate 3 may be used to adjust the first connector portion 124 relative to the second connector portion 126. A coupling member 128 may be provided for securing the first connector portion 124 to the second connector portion 126 and is preferably applied centrally in a precise manner in order to stabilize the first and second connector portions 124, 126. Coupling member 128 may be a threaded component, hook, latch, pin, nail, wire, tether, or combinations thereof. In an exemplary embodiment, coupling member 128 is a threaded component, such as a rivet, bolt or screw, preferably a lock screw having a snap off head. A Vernier scale option may be used to generate the best precise fit, but other adaptations may be used, with the most important requirement being that a secure fit is created. Vertebral plate 3, including connector portions 124, 126 may be loaded with graft material and may be contoured or sized to accommodate the specific graft or implanted material size. In one possible alternative embodiment, the connector portions may be curved or may be straight with a rise to accommodate the anatomy of the vertebra and/or the application of any bone graft material.

Vertebral plate 3 may be coupled to vertebra A1 and clamp 1 any manner. In an exemplary embodiment, vertebral plate 3 may include one or more apertures 10 that may be compatible with fastener 2 and/or other orthopedic structures. Apertures 10 may be arranged in any manner along the body of vertebral plate 3. By incorporating a plurality of apertures 10 spread out along vertebral plate 3, attachment system 100 may support or connect to other attachment systems 100 and/or other orthopedic structures situated in various different locations. Additionally, apertures 10 may have a variety of different sizes and/or shapes so that vertebral plate 3 may be compatible with different fasteners 2 and/or orthopedic structures.

As shown in the exemplary embodiments of FIG. 8, vertebral plate 3 may be anchored to the vertebral lamina or the posterior arch A3 of a C1 vertebra A200 by inserting fastener 2 through aperture 10 of vertebral plate 3, vertebra A1 and the dorsal and/or ventral apertures 8 of clamp 1. Vertebral plate 3 may be located between clamp 1 and vertebra A1. Alternatively, as shown in FIG. 6, clamp 1 may be located between vertebral plate 3 and vertebra A1.

Vertebral plate 3 may be fabricated from any high strength and biocompatible material. In an exemplary embodiment, vertebral plate 3 may be fabricated from any material having sufficient material and mechanical properties for load bearing applications, such as spinal stabilization. The material used to fabricate vertebral plate 3 may include a biocompatible metal, metal alloy, ceramic, polymer, such as a polymer from the polyaryl ether ketone family (PAEK) family, such as polyether ether ketone (PEEK) or polyether ketone ketone (PEKK), or composite material. Preferably, the material may include a metal alloy, such as stainless steel and/or titanium. Optionally, the surface of vertebral plate 3 may be treated to adjust the frictional, wear or biocompatibility properties of vertebral plate 3. In an exemplary embodiment, at least one portion of vertebral plate 3 may be coated with a material, shaped and/or textured to limit a range of motion of vertebral plate 3 relative to the vertebra A1 and/or clamp 1. In another embodiment, vertebral plate 3 may be coated with a material to minimize wear of vertebral plate 3 and/or facilitate osteointegration.

Optionally, the invention may further include a connector assembly 11 that may be used to removably couple vertebral plate 3 of attachment system 100 to other attachment systems 100 and/or other orthopedic structures to enable a wide variety of applications, including fusing two or more vertebrae and/or the occipitocervical junction. Connector assembly 11 may include any suitable fastening mechanism or structure.

In the exemplary embodiments of FIGS. 6 and 9, connector assembly 11 may include at least one system fastener 12, such as a threaded component, hook, latch, pin, nail, wire, tether, or combinations thereof that may be affixed to attachment system 100; preferably, system fastener 12 may be a threaded component, such as a screw, rivet or bolt. System fastener 12 may include a post 14 having a slot 15 for receiving a connection member 13. The device may be modular, wherein post 14 may include one or more slots 15 for retaining connection member 13. Additionally, system fastener 12 may be selectively inserted in a number of different apertures 10 of vertebral plate 3. Apertures 10 may have different sizes and/or shapes and may also be oriented in different directions relative to one another to accommodate different system fasteners 12 and to enable a wide variety of applications.

Connector assembly 11 may further include at least one connection member 13, such as a supporting rod, which may be used to couple one or more attachment systems 100 to each other and/or to other orthopedic structures anchored to different regions of the spinal column or cranium. In an exemplary embodiment, connection member 13 may be angled and/or contoured to enable connection with orthopedic structures located at different positions. Additionally, connection members 13 may be oriented, angled, or contoured to minimize or eliminate injuries, such as ventral brainstem compression. Connection members 13 may also include an optional pre-established rise option to accommodate the non-linearity of the level of the posterior arch A3 of the C1 vertebra A200 relative to other orthopedic structures and/or other anatomical surfaces. Connection member 13 may be secured within slot 15 using a system lock 16, such as a threaded component, hook, latch, pin, nail, wire, tether or combinations thereof. In an exemplary embodiment, system lock 16 may be a threaded component such as a screw, rivet, bolt, or nut.

Figure 12A:
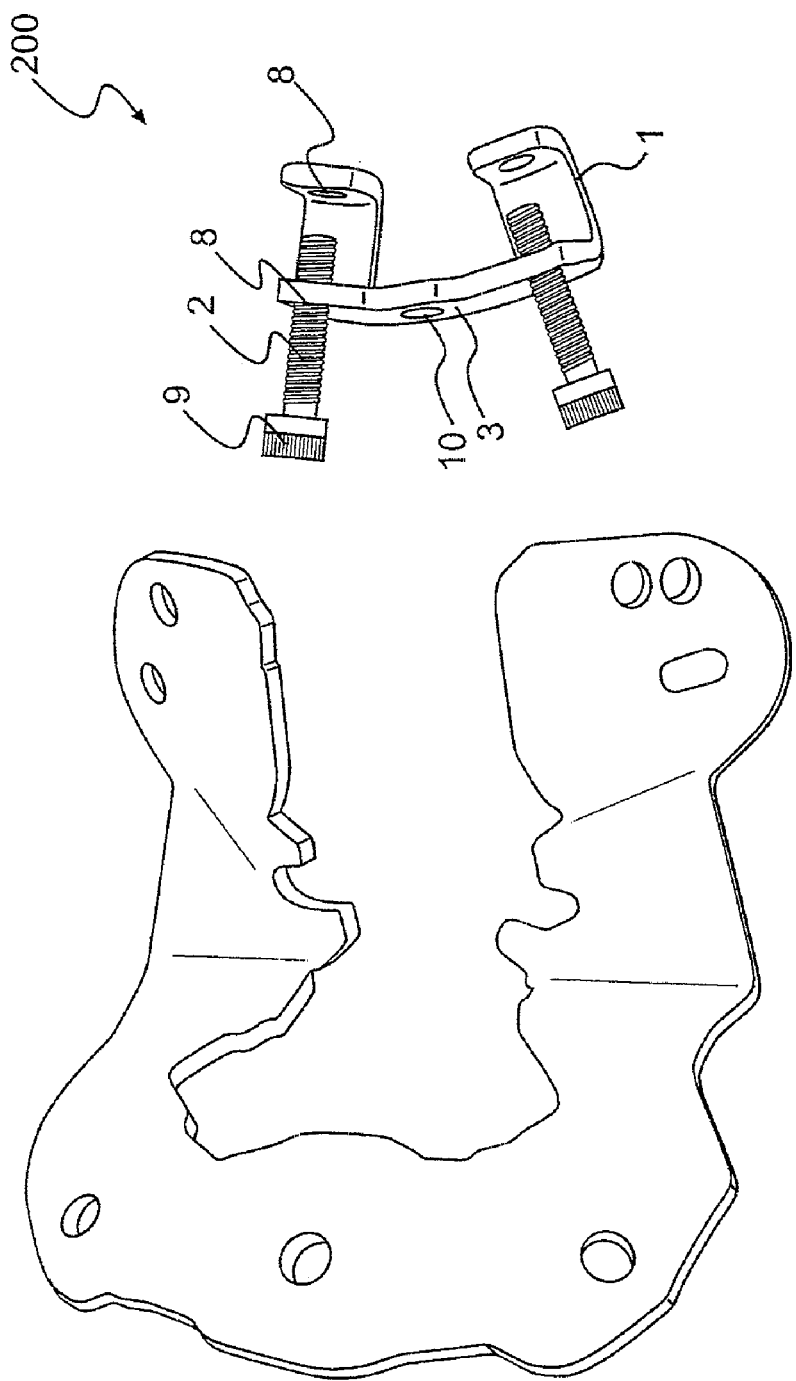
FIG. 12(a) is a perspective view of an attachment system wherein the clamps and plate are constructed as an integral device.
Figure 12B:
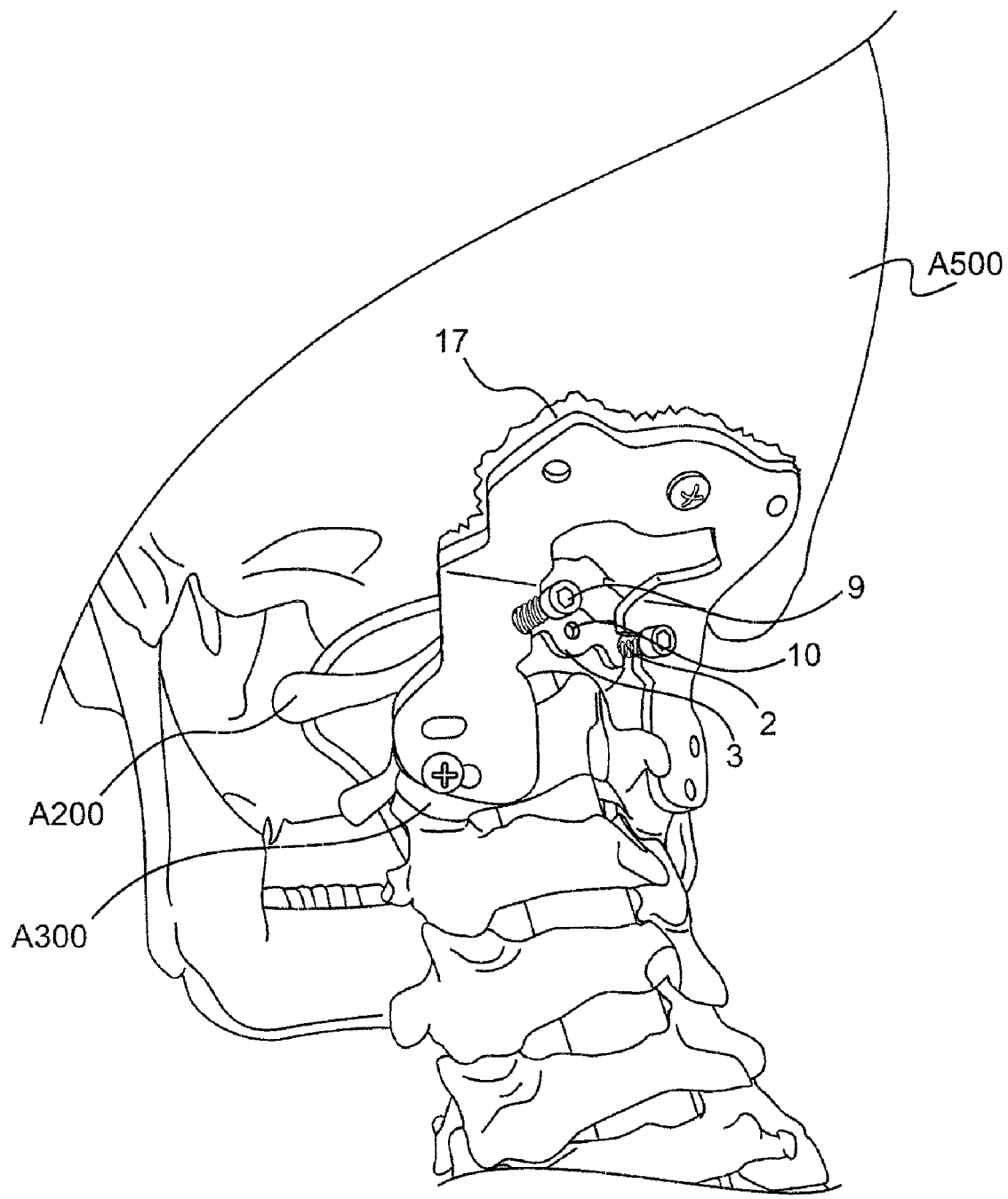
FIG. 12(b) is a perspective view of the attachment system of FIG. 12(a) fastened to an occiput plate.
Figure 12C:
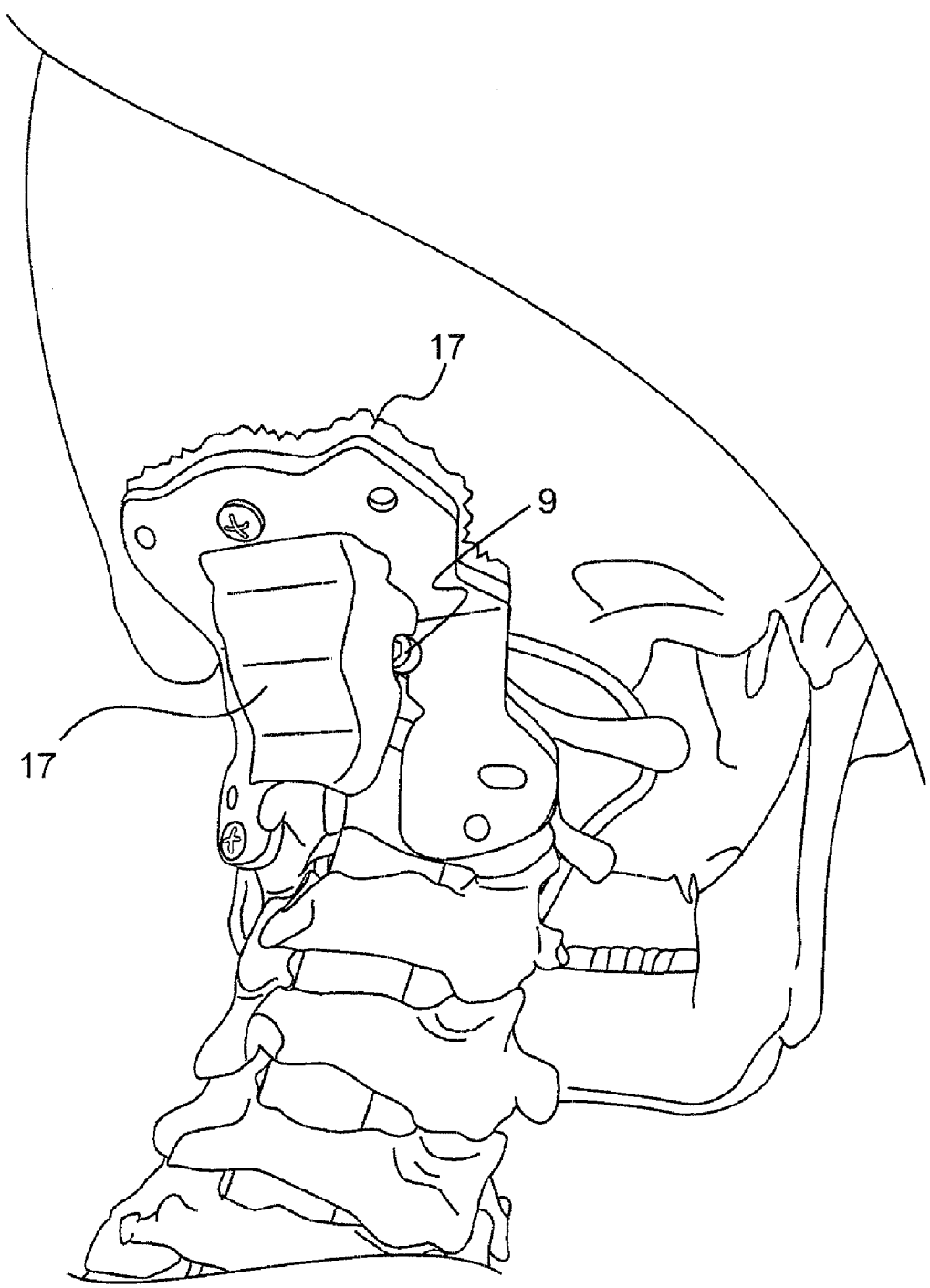
FIG. 12(c) is a perspective view of the attachment system of FIG. 12(a) with an applied bone graft material.

In the exemplary embodiment shown in FIG. 6, system fastener 12 may be directly coupled to attachment system 100 by passing through vertebral plate 3 at aperture 10 and/or vertebra A1. In another exemplary embodiment, FIGS. 12(a)-12(c) depict an exemplary attachment system 200 wherein system fastener 12 may be fastener 2. These figures show an occiput plate fastened directly to a vertebra A1 using system fastener 12, which also functions to couple vertebral plate 3 to vertebra A1. This dual function of system fastener 12 significantly increases the efficiency and speed of surgical procedures. In another exemplary embodiment, system fastener 12 may be a triple screw which possesses three functional portions along the length of the screw: a threaded portion for attachment to bone; a threaded or non-threaded portion to engage vertebral plate 3, and a threaded or non-threaded portion to engage connection member 13. The triple screw may provide increased stability by virtue of the combined fixation of the screw within vertebral plate 3 and vertebra A1.

Connector assembly 11 may be constructed from any high strength and biocompatible material. In an exemplary embodiment, connector assembly 11 may be fabricated from any material having sufficient material and mechanical properties that would enable load bearing applications, such as spinal stabilization. The material used to fabricate connector assembly 11 may include a biocompatible metal, metal alloy, ceramic, polymer, such as a polymer from the polyaryl ether ketone family (PAEK) family, such as polyether ether ketone (PEEK) or polyether ketone ketone (PEKK), or composite material. Preferably, the material may include a metal alloy, such as stainless steel and/or titanium. Optionally, the surface of connector assembly 11 may be treated to adjust the frictional, wear or biocompatibility properties of connector assembly 11. In an exemplary embodiment, at least one portion of connector assembly 11 may be coated with a material, shaped and/or textured to limit a range of motion of connector assembly 11 relative to the vertebral plate 3. In another embodiment, connector assembly 11 may be coated with a material to minimize wear and/or facilitate osteointegration.

The modular attachment system of the present invention may be operatively assembled and customized to enable a wide variety of applications and to create a custom fit for each patient. For example, the attachment system may include a combination of any number of clamps 1, fastener 2, vertebral plates 3, and connector assemblies 11 having any of the above discussed configurations, shapes or dimensions. Clamp 1, vertebral plate 3 and fastener 2 of exemplary attachment system 100 may be assembled during surgery. Alternatively, as shown in the exemplary attachment system 200 of FIG. 12(a), one or more clamp 1 and vertebral plate 3 may be pre-fabricated as an integral device and subsequently fastened to vertebra A1 using fastener 2 during surgery. Any orthopedic structure, such as a cranial and/or vertebral plate, may be fastened to attachment system. FIGS. 6 and 10(a) show an occipital plate anchored to an attachment system 100, 200, enabling stabilization of the occipitocervical junction.

The attachment systems of the present invention provides numerous advantageous over spinal fixation systems of the prior art. Because the attachment system may be located on the posterior portion of any vertebra, such as the posterior arch A3 of the C1 vertebra A200, it encumbers only the dorsal aspect of vertebra A1 and therefore does not substantially interfere with fusion or the major tension forces exerted during flexion of the neck. Typically the posterior surface of the C1 vertebra A200 is the least acceptable locus of fusion because of the high shear over the posterior surface in flexion, extension and rotation; the major loading forces in extension occur on the cranial and caudal surfaces of the C1 vertebral arch. The attachment system is also advantageous because it may have a unique structural configuration that is: compatible with a posterior region of vertebra A1, sufficiently thin to minimize the risk of neural or spinal cord compression, and/or does not significantly weaken the vertebra to which it is fastened. Additionally, because the attachment system may also be formulated as a modular kit including a plurality of clamps 1, fastener 2, vertebral plates 3 and connector assemblies 11 of varying sizes and configurations, it may be customized for each application and/or patient. Furthermore, the attachment system provides an effective, fast and safe means for vertebra attachment.

II. Method

An exemplary embodiment of the vertebra attachment method of the present invention may be used to enable a wide variety of spinal stabilization applications, including fusing the occipitocervical junction. The method may involve exposing the posterior occipitocervical junction and exposing the posterior arch A3 of C1 vertebra A200 without injuring the vertebral vein or artery A12 in the vertebral artery sulci. Before proceeding with the operation, the surgeon may check the CT or MRI to ensure that there is no stenosis at the level of C1 vertebra A200.

Figure 13:
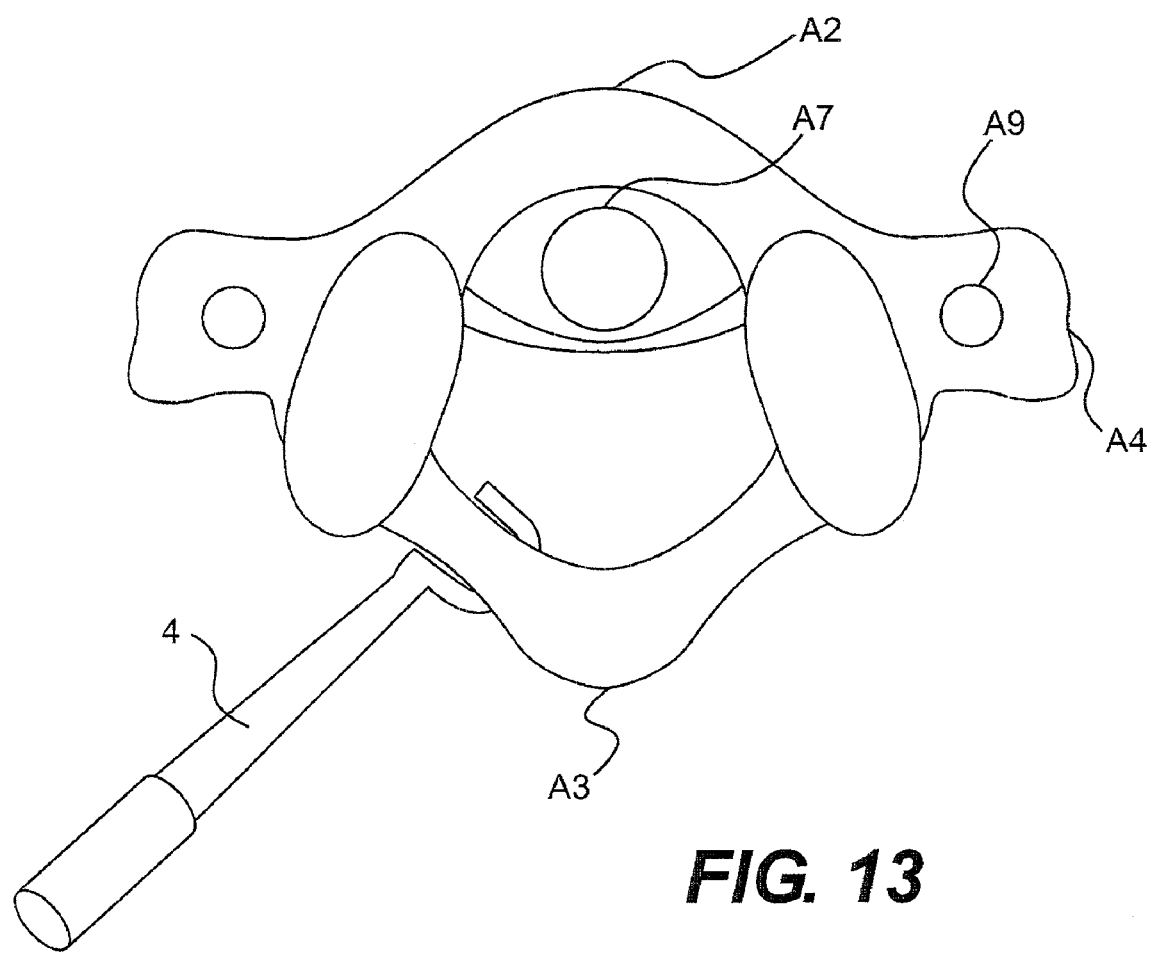
FIG. 13 shows an apparatus for testing trial clamps.

A curved instrument 4, such as a curette, as shown in FIG. 13, may be used to open the plane ventral to the posterior arch A3. The same curved curette serves as a trial template for the clamp to be fitted around the posterior arch A3 of a patient, in order to select the most appropriately sized clamp 1 for implantation. The selected clamp 1 may be inserted approximately 10-15 mm on one side of the midline of posterior arch A3 by friction fitting clamp 1 around a portion of posterior arch A3. A second clamp 1 may be inserted approximately 10-15 mm on the opposite side of the midline. Optionally, a third clamp 1 may be placed at the midline of posterior arch A3. In instances where only one clamp 1 is used to anchor vertebral plate 3 to vertebra A1, clamp 1 may be inserted at the midline. Vertebral plate 3 may be inserted between the posterior vertebra and the clamps 1, as shown in FIG. 8, or placed above clamps 1, as shown in FIG. 6. One or more apertures 10 of vertebral plate 3 may then be aligned with one or more apertures 8 of clamp pair 1. Alternatively, one or more clamps 1 and vertebral plates 3 may be constructed as an integral device and positioned on posterior arch A3 of C1 vertebra A200.

As shown in FIG. 6, after orienting clamp 1 and vertebral plate 3 on vertebra A1 as desired, the surgeon may drill at least one hole at aperture 8 of clamp 1 that at least partially penetrates posterior arch A3 to an appropriate depth. In an exemplary embodiment, the hole may penetrate the full thickness of posterior arch A3 of the C1 vertebra A200 or the full thickness of the lamina A19 of a lower vertebra. A fastener 2 may then be inserted through the hole and the dorsal and/or ventral apertures 8 of clamp 1. In an exemplary embodiment, fastener 2 may be optionally further secured to clamp 1, vertebral plate 3 and/or vertebra A1 with lock 9.

Alternatively, as shown in FIG. 7(d), after orienting clamp 1 and vertebral plate 3 on vertebra A1 as desired, fastener 2 may be inserted through an aperture 10 of vertebral plate 3 and through the dorsal and/or ventral apertures 8 of clamp 1. In this embodiment, fastener 2 does not penetrate vertebra A1 but rather secures clamp 1 and vertebral plate 3 to vertebra A1 by functioning as a clasp or latch that passes adjacent to a portion of vertebra A1, thereby minimizing trauma and vertebra erosion. As discussed above, fastener 2 may also include a lock 9 to prevent loosening under applied physiological loads.

After inserting the first fastener 2, the location of a second clamp 1 may be readjusted relative to vertebra A1 and/or aperture 10 of vertebral plate 3 as desired. At least a second aperture 8 and second aperture 10 may be aligned, and another fastener 2 may be attached in a similar manner using the previously discussed methods. Lock 9 may also optionally further secure the retention of vertebra A1.

Connector assemblies 11 may be used to couple one or more attachment systems to one another or to other orthopedic structures or assemblies. At least one system fastener 12 may be inserted through an aperture 10 of vertebral plate 3. In an exemplary embodiment, system fasteners 12 are only coupled to vertebral plate 3 and do not penetrate vertebra A1. Alternatively, a hole may be drilled at the location of aperture 10 so as to at least partially penetrate vertebra A1. System fastener 12 may be inserted through aperture 10 and the hole in vertebra A1 to further secure the connection between the attachment systems and/or other orthopedic structures.

Figure 11:
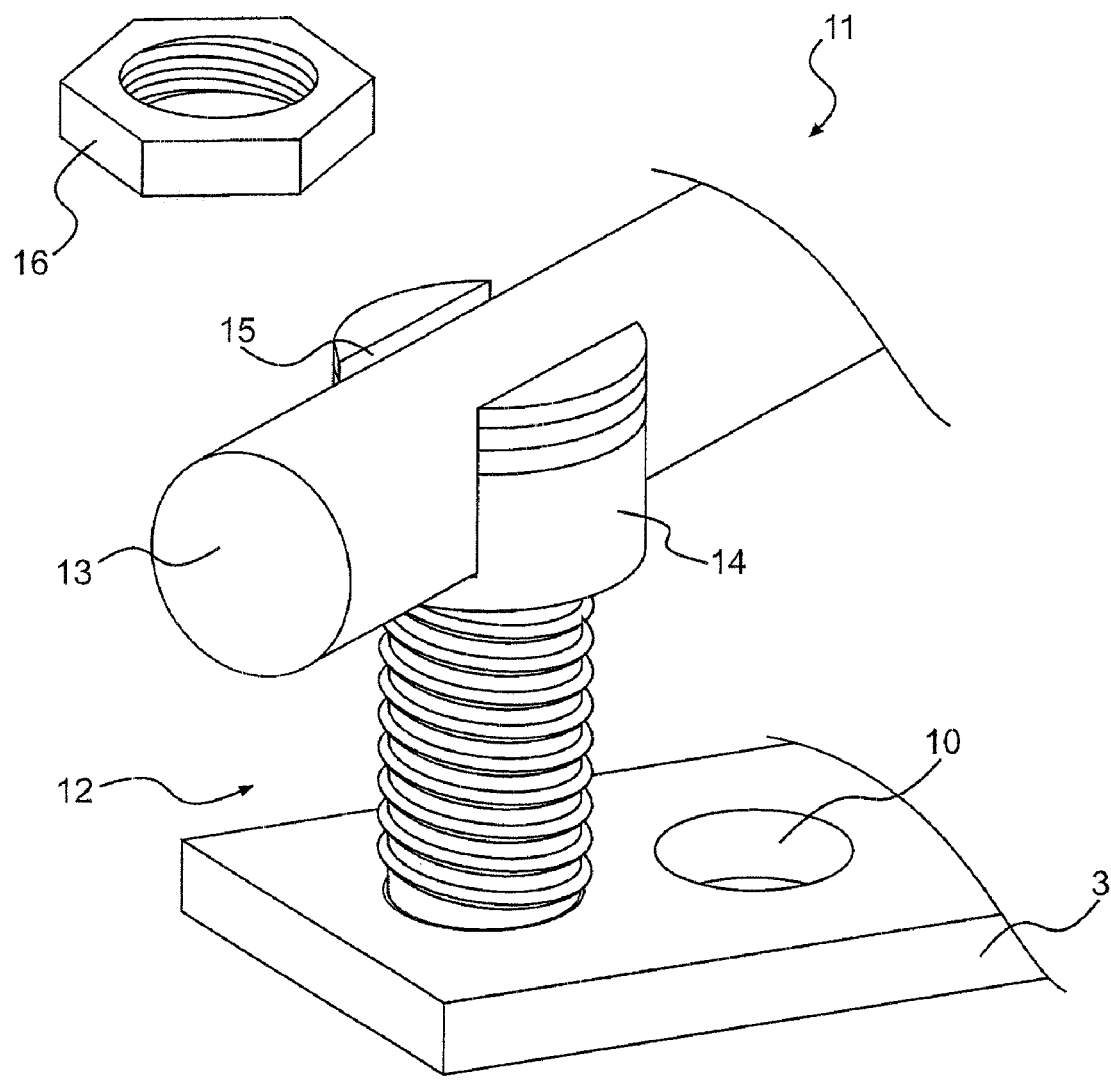
FIG. 11 is a perspective view of a connector assembly placed within an aperture of a variable screw head.

As shown in FIG. 11, a connection member 13 may be inserted into at least one slot 15 of post 14. A system lock 16 may be fastened adjacent to or on top of the arms of post 14 to securely retain connection member 13. In an exemplary embodiment, system fastener 12 may be rotated relative to vertebral plate 3 to adjust the orientation of connection member 13 relative to attachment systems 100 and/or other orthopedic structures. As shown in FIG. 6, one portion of the connection member 13 may be coupled to attachment system 100, and at least one other portion may be fastened to another attachment system and/or other orthopedic structures, such as an occipital plate. One or more connection member 13 may be fastened to multiple attachment systems and/or occipto cervical device to create a fixation assembly extends along one or more vertebrae A1.

An osteogenic bone graft material 17, may be applied to the junctions between attachment system 100 and connector assembly 11 to facilitate bone fusion. In an exemplary embodiment, osteogenic material 17 may include, without limitation, autograft, allograft, xenograft, demineralized bone, synthetic and natural bone graft substitutes, such as bio-ceramics and polymers, and osteo-inductive factors. In an exemplary embodiment, osteogenic material 17 may include a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material. Additionally, osteogenic material 17 may also be applied partially along or completely cover any surface of clamp 1, fastener 2, vertebral plate 3, and/or any other orthopedic structure to which attachment system 100 is directly or indirectly connected to promote osteoblast generation and facilitate bone fusion. As shown in FIG. 12(c), bone graft material 17 may be placed above, below or on any surface of attachment system 100 as well as any corresponding orthopedic structure.

In addition to stabilizing the occipitocervical junction, a similar method may be used for fusing any two or more spinal vertebrae. In general, the method may involve exposing the general region of the spinal column to be stabilized or fused, and exposing the specific vertebral region to which an attachment system of the present invention may be affixed. The attachment system may be fastened to the dorsal elements of the vertebra similar to the above discussed C1 attachment method. In an exemplary embodiment, the attachment system may be fastened to a region that is safely distanced from the spinal cord, spinal nerve roots, vertebral artery A12 and/or vertebral vein so as to avoid severing, compressing, impinging or otherwise injuring the these spinal components. In one embodiment the attachment system may be fastened to a posterior region, such as the spinous process pedicle and lamina, as shown in FIG. 9. The attachment system may be coupled to at least one other attachment system and/or at least one other orthopedic structure, which is attached to another vertebra, using connector assembly 11.

The vertebra attachment system and method of the present invention may be used to enable stabilization and/or fusion of the junction between any spinal vertebrae and/or the occipitocervical junction of humans as well as animals. Specifically, the invention may be used to enable spinal or occipito-cervical instability due to trauma or chronic spinal conditions, such as degenerative spinal diseases, metabolic spinal diseases, congenital spinal diseases, endocrinological spinal diseases, neoplastic or infectious spinal diseases, or cancer. Examples of chronic spinal conditions which may be treated in part using the vertebra attachment system of the present invention include degenerative diseases, such as systemic lupus erythematosis and rheumatoid arthritis, and metabolic conditions, such as osteomalacia, osteogenesis imperfecta, hyperparathyroidism, Ricket's Disease and Hurler's Disease; which cause basilar invagination. Other examples of conditions which may be assisted with the present invention may include congenital conditions, such as Down's syndrome and Morquio's Syndrome or miscellaneous conditions, such as Chiari Malformation, assimilation of the atlas, Klippel-Feil syndrome, condylus tertius, hypochordal bow, dystopic odontoideum, which may cause compression of the upper spinal cord or brainstem.

III. Exemplary Occipitocervical Junction Stabilization System

Figure 14:
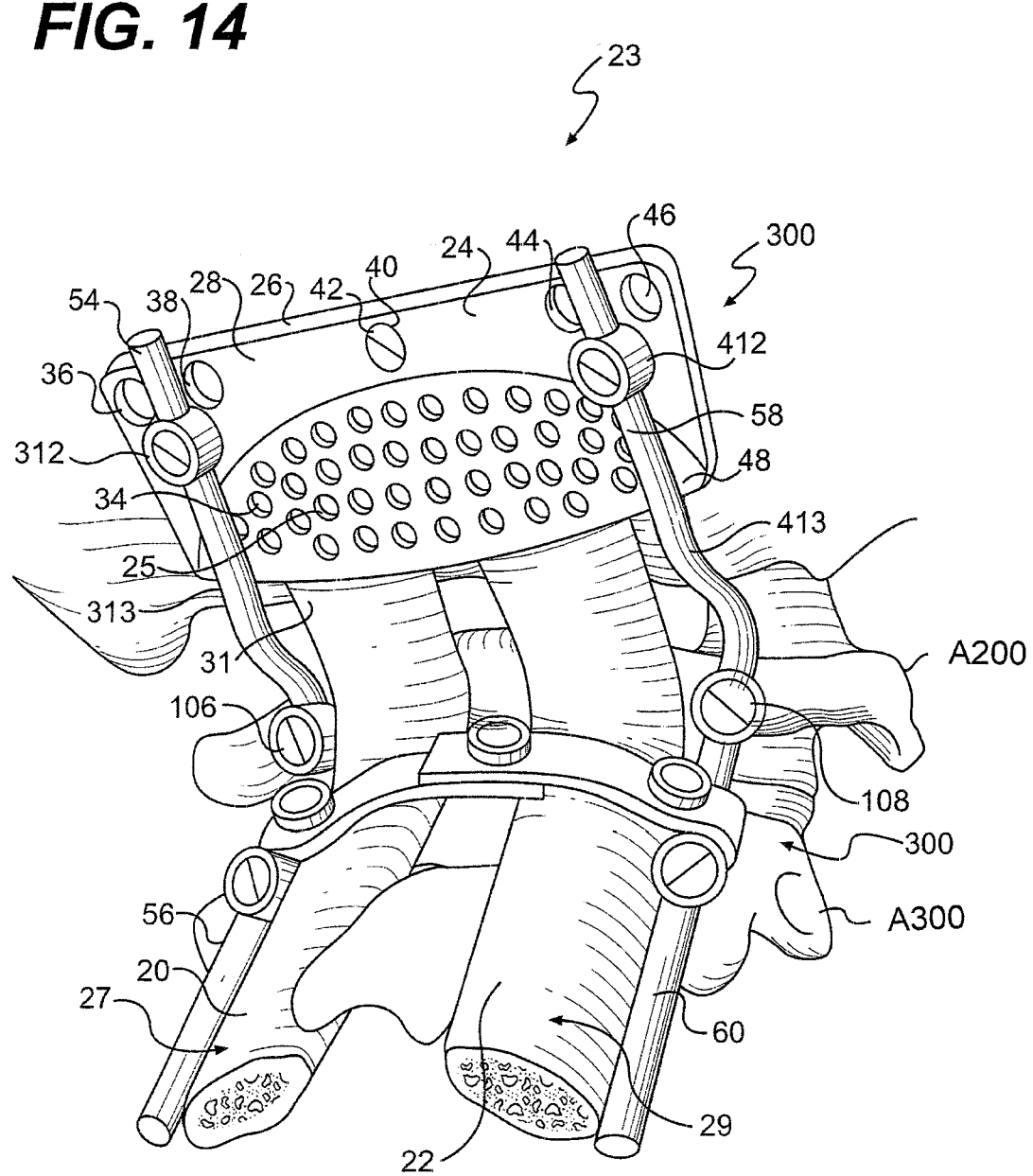
FIG. 14 is a perspective view of a system for effecting fusion of the human occipitocervical junction according to a preferred embodiment of the invention.

FIG. 14 shows one embodiment of attachment system 300 used in conjunction with an exemplary spinal system 400 to stabilize the occipitocervical junction. Attachment system 300 of the present invention differs from exemplary attachment systems 100, 200 in that: clamps 301, 401 may be configured to retain connection members 313, 413 rather than directly retaining a portion of vertebra A1 between its arms 116, 118 and fasteners 302, 402 in this embodiment, need not contact the vertebral body. Notably, it is envisioned that attachment systems 100, 200 may also be used in conjunction with the exemplary spinal system 400.

As shown in FIG. 14, spinal system 400 may include a first bone forming material based structural member 27 and a second bone forming material based structural member 29. The two bone forming material based structural members 27, 29 may be bone grafts that are harvested from another part of the patient's body, such as a rib, grafts from a cadaver, or a material that is constructed and arranged to facilitate the growth of bone. The invention is accordingly not limited to bone, but may use bone substitutes or non-osseous materials to accomplish long-term fixation of the cranium to the spine. For example, the two bone forming material based structural members 27, 29 may be fabricated from a metallurgically bonded porous metal coating that is constructed and arranged to encompass and contain bone graft material, such as TRABECULAR METAL™ material by Zimmer Inc. of Warsaw, Ind.

The two bone forming material based structural members 27, 29 could alternatively be fabricated from a bone forming material such as a bone substitute that is fabricated from a collagen base and contains bone forming materials, or bone enhancing chemicals. Thus a bone forming material could be embodied as a fabricated mesh that functions as a bone conductor into which bone growth would occur, or as a bone-like medium such as coralline hydroxyapatite, which serves as an osteoconductor for blood vessel formation and subsequent deposition of bone, which could be injected or poured into the space between the bones to be fused.

Alternatively, the bone forming material could be embodied as a metallic mesh-like substance that encourages or enables bone growth, such as tantalum mesh, which could be molded to fit into the space between the occiput and the spine, a bone allograft or a xenograft.

The first bone forming material based structural member 27 has a first portion 31 that is positioned and biased against the cranial bone so as to promote bone fusion between the cranial bone and the first bone forming material based structural member 27. Accordingly, the second bone forming material based structural member 29 has a first portion 27 that is positioned and biased against the cranial bone so as to promote bone fusion between the cranial bone and the second bone forming material based structural member 29. In one embodiment, these functions of positioning, support, biasing and promotion of fusion are effected through the use of an occipital connection system 23, which will be described in greater detail below.

The bone forming material based structural members 27, 29 preferably each have transverse cross-sectional area of approximately 1 cm².

The first and second bone forming material based structural members 27, 29 further respectively have second portions 20, 22 that are positioned and biased against at least one cervical vertebral body of a human cervical spine so as to promote bone fusion between the cervical vertebral body and the respective bone forming material based structural member 27, 29. This function may be effectuated through the use of attachment system 300. Preferably, spinal system 400 facilitates a fusion between said bone forming material based structural members 27, 29 and both the C1 and C2 cervical vertebral bodies A200, A300.

Figure 15:
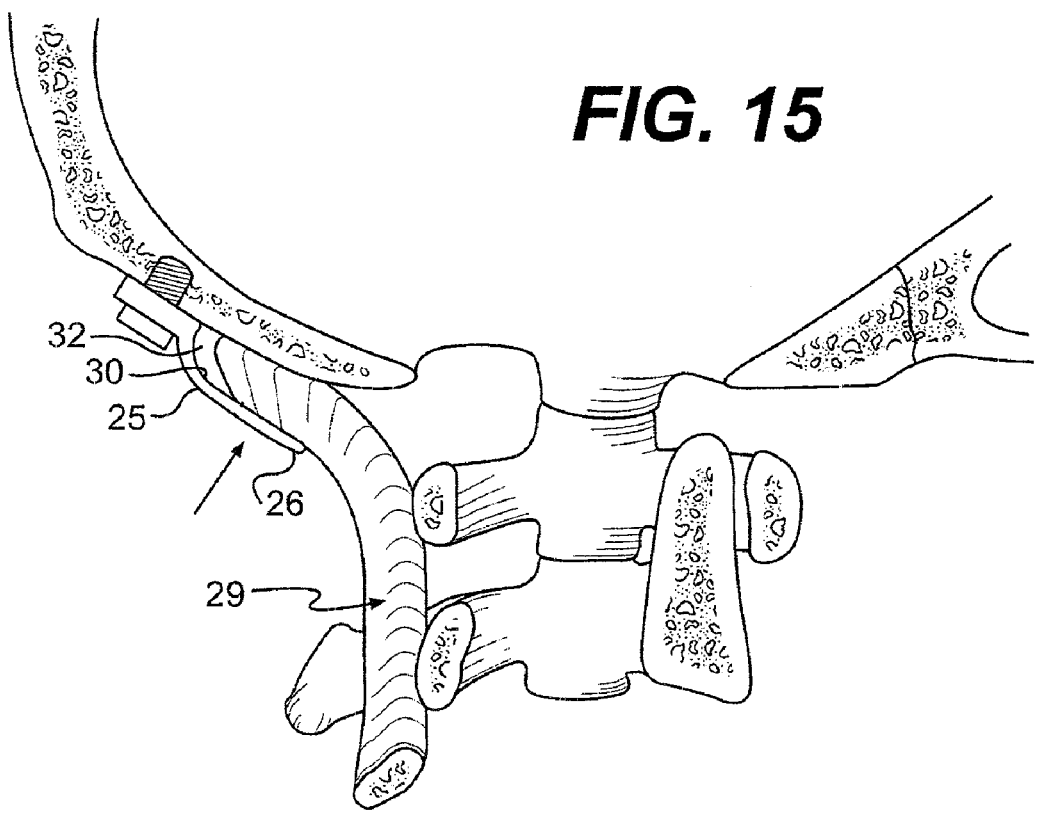
FIG. 15 is a cross-sectional view of a portion of the system that is depicted in FIG. 14.

Spinal system 400 may further include an occipital connection system 23, which includes a cranial plate member 24 that is shaped so as to define an outer edge 26, an outer surface 28 and an inner surface 30, as is best shown in FIG. 15. Cranial plate member 24 is preferably shaped to define a graft accommodation space 32 between the cranial plate member 24 and the cranium A500. The graft accommodation space 32 is preferably defined in part by a flange 25, which is defined in the cranial plate member 24 by a portion of the cranial plate member 24 including the caudal portion of the outer edge 26 that is elevated away from the cranium A500 with respect to a portion of the inner surface 30 that is contacting the cranium, so that the graft accommodation space 32 is open to a space outside of the graft accommodation space 32.

The cranial plate member 24 is preferably a monolithic plate, composed of metal, polyetheretherketone (PEEK), bioabsorbable compound, bone or bone substitute. The cranial plate member 24 preferably has a thickness of more than 1 mm and less than 1 cm at the edges, and may vary in thickness. For instance the edge 26 of cranial plate member 24 may be 1 mm, but the central part may be increased to 15 mm. The cranial plate member 24 may be ovoid, rectangular, polyhedral or a composite of straight edges and curves, and thus is not confined to a particular shape or perimeter. The cranial plate member 24 may be coated or made of a bio-compatible material, or coated with substances which are known to improve or accelerate surface attachment, or to promote bone fusion. The cranial plate member 24 may or may not contain a metallurgically bonded porous metal coating. The cranial plate member 24 may be slightly curved so as to be complementary to the curve of the cranium, or may be flat, or may undergo a contouring process by the surgeon or assistant at the time of surgery.

The flange 25 is an elevated contour arising from the cranial plate member 24. The flange 25 makes available for fusion the underlying cranial surface; the elevation of the flange 25 exposes the cranial bone surface to the overlying bone graft. The flange 25 may be constructed from the same material as the remainder of the cranial plate member 24, or it may be a constructed as a separate component that is attachable to the cranial plate member 24. The purpose of the flange 25 is to incorporate, to enclose or to provide a fulcrum in which bone graft materials or substitutes, or other materials, may be held for the purpose of achieving a bone union or other permanent rigid or non-rigid attachment between the cranium and the spine.

The flange 25 may be non-perforated or may include one or multiple perforations and could be composed of a mesh or mesh-like construction. The flange 25 is preferably perforated to allow in-growth of bodily tissue or blood vessels. The flange 25 has a perforated plus non-perforated surface area of more than 15% of the area of the plate member component.

The thickness of the flange 25 is 0.5 to 5 mm thickness. The purpose of the flange 25 is to entrap the bone forming substances or other structural members in close union with the underlying cranium and to facilitate in the case of bone, morphogenesis through application of load, that is, through pressure and stabilization of the bone forming substances to enhance the milieu favoring new bone formation. The flange 25 may be capable of being mechanically altered in shape to further compress the graft.

The flange 25 will preferably rise from the plane of the portion of the cranial plate member 24 that contacts the cranial bone for a distance that is more than about 5 mm, to allow placement of a thickness of material that is adequate to provide stability for growth. It is envisioned that malleable, or woven-bone forming substrates could be used to promote fusion, or indeed provide the scaffolding itself for fusion. Conversely, other materials could be used beneath the flange 25 to provide non-osseous, non-rigid fixation.

Flange 25 will preferably allow the passage or inset of rods, plates or other materials for connecting the cranial plate to the spine. The purpose of this is to lower the profile of the rod, and to minimize the potential deformity of overlying tissue. Thus, a rod may pass through a perforation in a mesh of the flange to connect to the triple screw. Alternately, the flange 25 may have a groove, a pop-out section or perforations to allow passage of the stabilization element connecting cranium to spine.

In an alternative embodiment, the flange 25 might serve to provide attachment for a non-osseous union between the cranium and spine. The flange 25 thus may have both a physiological function and a mechanical function.

Flange 25 is envisioned in the preferred embodiment to arise from the lower aspect of the cranial plate member 24. However, alternate embodiments would allow positioning of a single or multiple flanges 25 in various locations, such as the middle, the upper or the sides of the cranial plate member 24. Thus the flange should not be construed to exist only as an elevation from the lower edge of the cranial plate member 24, but, for instance, may be centered on the cranial plate member 24; a rim of cranial plate member 24 could thus fully encompass flanges 25.

Whilst the preferred embodiment of the flange 25 is curved to minimize its profile by conforming to anatomic contour, alternate forms may include box-like constructs, or even a multiplicity of shapes and sizes that could be chosen for a given application, and then be secondarily attached to the cranial plate member 24. For example, a low profile, curved flange 25 could be applied to the cranial plate member 24 over the cranium of an asthenic child; another embodiment, for a larger person, may be a larger box-like adaptation designed to facilitate the incorporation of a more rectangular, synthetic bone-forming substance or other non-osseous compound. It is thus envisioned that flange 25 may offer a multiplicity of options to enable a wide variety of applications that may be patient customized.

As is shown in FIG. 15, the first portion 27 of the second bone material based structural member 29 is preferably positioned within the graft accommodation space 32 defined by the flange 25 so that the inner surface 30 of the cranial plate member 24 is biased to provide compressive pressure against the second bone material based structural member 29. This compression will facilitate bone fusion between the second bone material based structural member 29 and the cranium A500.

As FIG. 14 shows, the first portion 31 of the first bone material based structural member 27 is similarly positioned within the graft accommodation space 32 and impressively biased against the cranial bone to promote bone fusion.

Alternatively, the cranial plate member 24 could be fabricated so as to include more than one graft accommodation space, so that each of the two structural members 27, 29 could be separately positioned within different accommodation spaces that are defined by the inner surface 30 of the cranial plate member 24.

The inner surface 30 of the cranial plate member 24 is preferably composed of a material that promotes bone fusion. This could be accomplished by coating the cranial plate member 24 with anyone of a number of conventional bone growth promoting substances or by fabricating the cranial plate member 24 from a porous material that is constructed and arranged to encompass and contain bone graft material, such as TRABECULAR METAL™ material. Cranial plate member 24 further preferably has a plurality of perforations 34 defined therein. Perforations 34 preferably have a minimum diameter of at least 400 microns, so as to best facilitate the growth of blood vessels within the newly formed bone tissue. A portion 48 of the outer surface 28 of the cranial plate member 24 may be grooved in order to accommodate instrumentation, as will be described in greater detail below.

Cranial plate member 24 preferably has a plurality of pre-drilled threaded mounting holes 36, 38, 40, 44, 46, 72 defined therein for facilitating attachment of the cranial plate member 24 to first portions 54, 58 of first and second connection members 313, 413 by means of first and second system fasteners 312, 412, respectively. The cranial plate member 24 will therefore preferably include manifold screw holes in order to permit the connection members 313, 413 to be secured to the cranial plate member 24 and locations that are most suitable for an individual patient.

A central screw hole 40 will serve to anchor a central plate screw 42. There may be multiple central screw holes 40. The central screw holes 40 may be positioned approximately in the midline of the patient's body and cranium in order to permit placement of screws into the thickest part of the skull, which usually runs from the inion to the opisthion. These holes 40 may be threaded, partially threaded or not threaded.

On each side of the midline, cranial plate member 24 may have at least one additional hole 38, 44, 46, 72 which is positioned to receive a screw, such as triple screw 70, which engages in the plate member and serves to anchor stabilization elements, such as rods, plates or other structures, from the cervical spine. Holes 38, 44, 46, 72 may cluster, may overlap, may be placed in an arc, or may be oriented contiguously or in separate locations. Holes 38, 44, 46, 72 may be placed around the edge of the flange 25, or on the flat portion of the cranial plate member 24. These holes may be reinforced with extra thickness and may be either threaded or non-threaded. Second portions 56, 60 of the first and second connection members 313, 413 are secured to the cervical spine of the patient, as will be described in greater detail below.

The central plate screw 42 provides primary attachment of the cranial plate member 24 to the skull. It is robust, cortically threaded, of variable length, preferably having a length within a range of about 7 mm to about 12 mm. The central plate screw 42 preferably has a thickness within a range of about 2 mm to about 10 mm, with a blunted end. It may have a spiral lock feature that locks the screw 42 into the cranial plate member 24, or not. It may be lagged to provide increased loading pressure on the cranial plate member 24, or not. It can be made of titanium alloy, of bone, or of a bone forming or bone compatible substance. For example, a ceramic, or hydroxyl-apatite composite or metal alloy/bone composite could be used.

In an alternative embodiment, a screw/rivet could be used in lieu of the central plate screw 42 for rapid application. The screw or screw/rivet would preferably have torque strength of greater than 35 inch lb and generate sufficient pullout strength to prevent dislodgement from the cortex. The screw or screw/rivet would be placed near the middle of the cranial plate member 24, and be fashioned to pass through the central screw hole 40 on the cranial plate member 24.

Figure 20:
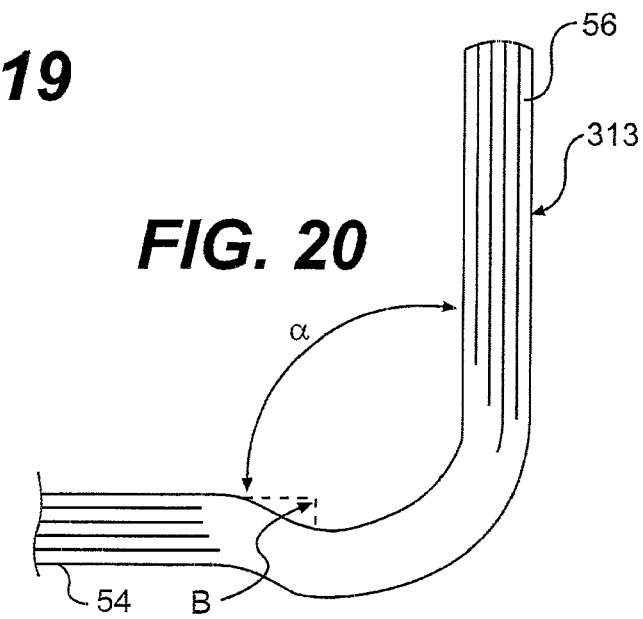
FIG. 20 is a side view of one component of the system that is depicted in FIG. 16.

The first and second connection members 313, 413 provide the main structural connection between the cranium A500 and the upper cervical spine during the immediate postoperative period. Connection members 313, 413 are preferably standard titanium rods, approximately of 3-4 mm gauge, bent to conform to the correct craniospinal angle. The salient differences from other rods currently available are two-fold. The first is an angle reflecting the corrected reduction of the angle ($\alpha$ angle, FIG. 20) between the cranium and that of the spine; in the preferred embodiment this will be pre-set within a range of about 75° to about 90°. Accordingly, the first and second connection members 313, 413 are contoured to ensure a postoperative craniospinal relationship that confers a clivo-axial angle, i.e. the angle between the dorsum of the second cervical vertebra and the dorsum of the clivus, approaching about 145-165°, and more preferably about 155 to 165°.

Simultaneously, the degree of ventral brainstem compression should be rendered close to zero, by virtue of the reduction of angulation between the cranium and spine, and in some cases by the posterior translation of the cranium upon the spine.

Second, the craniospinal connection members 313, 413 will have a pre-established rise option (the α rise, FIG. 20), to accommodate the non-linearity of the level of the posterior arch A3 of the C1 vertebra A200 to the surface of the lamina A16 of the C2 vertebra A300 and lateral mass A4 of the C3 vertebra. Accordingly, the presence of the pre-established α rise will allow the connection members 313, 413 to contact the C1 and C2 laminae A16.

Figure 16:
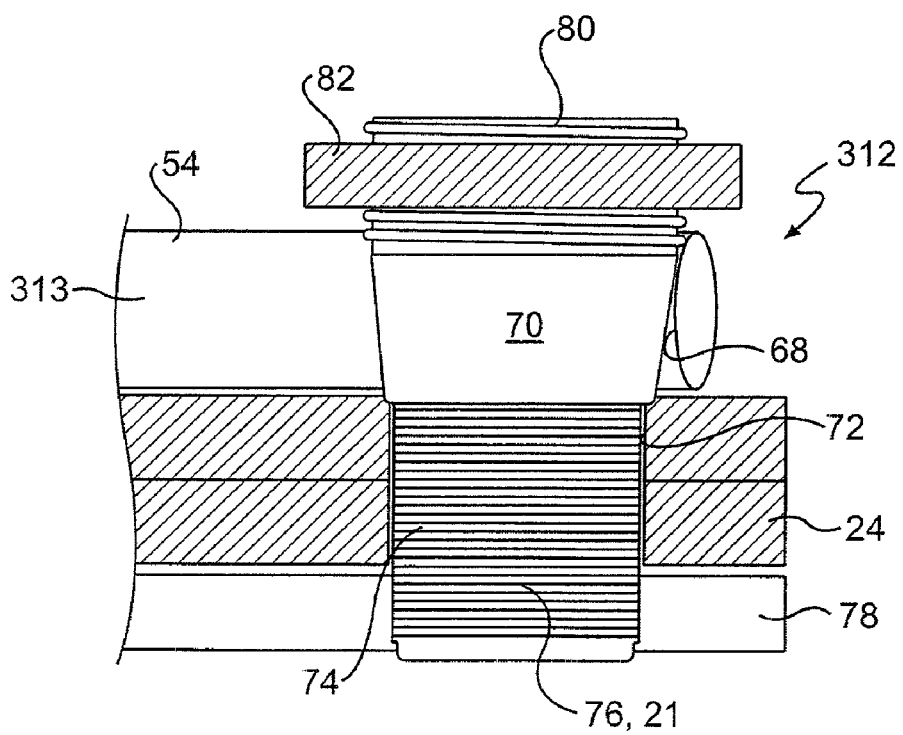
FIG. 16 is a cross-sectional view depicting a connector assembly that is constructed according to a preferred embodiment of the invention.

System fasteners 312, 412 are shown in greater detail in FIG. 16. In a preferred embodiment, an unthreaded hole 68 is defined in the first portion 54 of the first connection member 313 and a threaded hole 72 is provided in the cranial plate member 24. System fastener 312 advantageously includes a unique triple screw 70 that has a first threaded portion 70 at an intermediate section thereof that is sized and pitched to mate with the threaded hole 72 in the cranial plate member 24 and a second threaded portion 76 at a lower section thereof that is constructed and arranged to be screwed into the cranial bone 78.

Triple screws 70 have the unique characteristic of deriving stability from fixation within the skull, the cranial plate member 24 and around the rod or plate that connects the cranium to the spine. In addition, the triple screw 70 has a number of functions: first, it connects the plate to the cranium; second, it connects the cranium to the craniospinal connecting devices; third, it eliminates plate torque around the central screw 42. In so doing, it eliminates one of the steps common to all other craniospinal devices: that of an additional and independent means of attaching the cranial plate member 24 to the craniospinal rod or plate connector.

Triple screws 70 may possess three functional portions: a threaded portion for attachment to the cranial bone 78; a threaded or non threaded portion to engage the cranial plate member 24; and a threaded portion for attaching the connection member 313. The central or intermediate portion may be threaded to enhance binding to the cranial plate member 24 or non-threaded to allow a lag effect upon the cranial plate member 24 in order to allow the insertion of triple screw 70 to tighten the plate member down to the cranial bone 78, depending upon the requirements of the particular stabilization.

The triple screws 70 may be placed in one of many potential screw holes on each side of the cranial plate member 24, in order to accommodate to the variability of the system that attaches the cranium to the cervical spine. Whilst the triple screws 70 are shown in the upper portion of the plate member in the illustrated embodiment, they may in another embodiment be placed in the lower aspect of the cranial plate member 24. They are not limited to being positioned at lateral opposite sides of the cranial plate member 24, but may be placed near the middle of the cranial plate member 24. The triple screw 70 can be turned to any direction to accommodate the craniospinal rod or connector system.

The triple screw 70 will preferably be inserted through the cranial plate member 24 and screwed into the skull. The triple screw 70 will provide increased stability to the plate and rod system by virtue of the combined fixation of triple screw 70 within the cranial plate member 24 and the skull. The triple screw 70 may be threaded at the level of the skull with a cortical or cancellous thread or could in another embodiment utilize a rivet-type fixation. In any event, the internal portion of the screw is firmly fixated to the skull.

Figure 17:
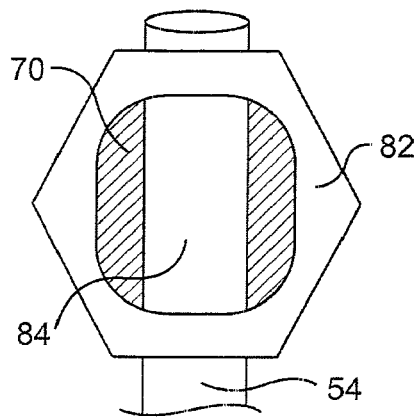
FIG. 17 is a top plan view of the connector assembly that is depicted in FIG. 16.

Triple screw 70 further includes a third threaded portion 80 at an upper portion thereof that is sized in pitch to mate with an internally threaded hexagonal nut 82. As is shown in FIG. 17, which provides a top plan view of the connector assembly 62, an upper surface of the triple screw 70 is provided with a slot for receiving a screwdriver blade.

Figure 18:
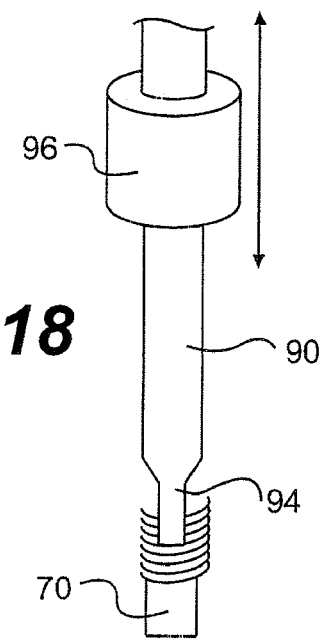
FIG. 18 is a perspective view of a fastening tool that is designed to be used in conjunction with the connector assembly that is depicted in FIG. 16, shown in a first operative position.
Figure 19:
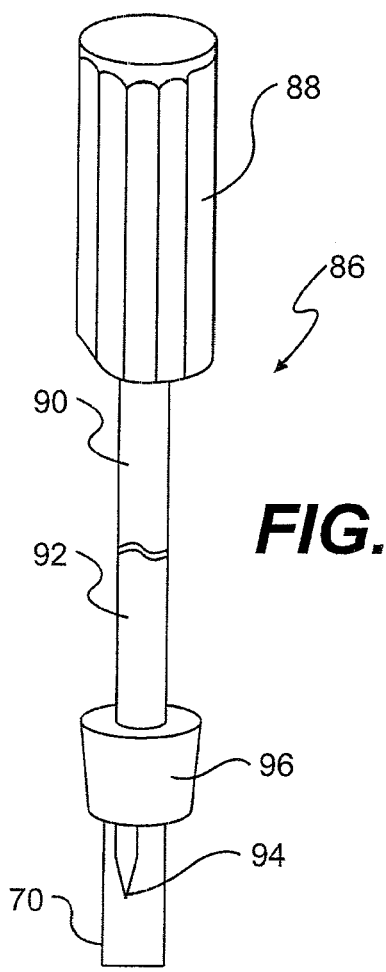
FIG. 19 is a perspective view of the fastening tool that is shown in FIG. 18, shown in a second operative position.

FIGS. 18-19 depict a unique tool 86 that is constructed and arranged to be used in conjunction with the connector assembly 62 and the triple screw 70. Tool 86 includes a handle 88 and a shaft 90 that may be provided with a universal joint 92 for accessibility purposes, e.g. to accommodate non-orthogonal placement of the screw. For instance, if access to the triple screw 70 is encumbered by a patient's corpulence, the screw may be inserted at an angle. A screwdriver blade 94 is provided at a distal end of the shaft 90 and is preferably sized and shaped to be effectively received by the slot 84 that is defined in the upper surface of the triple screw 70. Additionally, tool 86 preferably includes a sleeve 96 that is slidable upwardly and downwardly on the lower portion of the shaft 90 between a first retracted position that is shown in FIG. 18 and a second, extended operative position that is shown in FIG. 19. Sleeve 96 is shaped to define an internally threaded socket that mates with the external thread 80 of the triple screw 70. Sleeve 96 is further mounted to the shaft 90 so that it is prevented from rotating with respect to the shaft 90. Accordingly, a surgeon may use the tool 86 in the operative position that is shown in FIG. 18 in order to tighten the triple screw 70 with respect to the cranial plate member 24 and the cranial bone 78 with the sleeve 96 stabilizing the tool 86 with respect to the triple screw 70 and preventing the blade 94 from slipping out of the slot 84.

Referring now to FIGS. 21-22, spinal system 400 further incorporates an embodiment of attachment system 300 for positioning and biasing the second portions 20, 22 of the first and second bone forming material based structural members 27, 29 against at least one cervical vertebral body of a human cervical spine so as to promote bone fusion between the cervical vertebral body and the respective bone forming material based structural member 27, 29.

In one embodiment, the vertebral attachment system 300 includes a vertebral plate 303 that is positioned to compress the first bone material based structural member 20 and the second bone material based structural member 22 against a vertebral body such as the vertebral body C2 that is depicted in FIG. 21. The vertebral plate 303 may hold a graft material in close contact with the underlying spinal vertebrae to facilitate in-growth of blood vessels or other tissue, as is depicted in FIGS. 21-22. Additionally, the vertebral plate 303 stabilizes the two sides of the spinal system 400, connecting the respective connection members 313, 413 from one side to that of the other, thereby decreasing the potential for toggling.

Accordingly, the vertebral plate 303 is connected to the first structural connection member 313 at one portion thereof that includes a first clamp 301 for releasably clamping one end of the vertebral plate 303 to the first structural connection member 313. In one embodiment, the first clamp 301 includes a curved plate portion 116 that curves about most of the circumference of a first structural connection member 313. A fastener 302 extends through first and second holes that are defined in the curved plate portion 303 for tightening and loosening the first clamp 301 with respect to the first structural connection member 313.

Likewise, the vertebral plate 303 is connected to the second structural connection member 413 at a second portion thereof that includes a second clamp 402 for releasably clamping a second, opposite end of the vertebral plate 303 to the second structural connection member 413. The second clamp 402 includes a curved plate portion 118 that curves about most of the circumference of the second structural connection member 413. A fastener 402 extends through first and second holes that are defined in the curved plate portion 118.

The curved plate portions 116, 118 of the respective clamps 301, 401 may extend around the circumference of the respective connection member 313, 413 as viewed in transverse cross-section for an angular distance of at least three radians. In addition, the fasteners 302, 402 may be positioned on the medial side of the respective connection member 313, 413.

The vertebral plate 303 may be curved so as to be concave on a side thereof that is positioned to contact the first bone material based structural member 20 and said second bone based structural member 22.

The vertebral plate 303 further includes structure for adjusting a length of the vertebral plate 303, whereby a lateral spacing distance between said first and second laterally spaced structural connection members may be adjusted. The structure may include two separate components that are attachable to each other, specifically a first curved connector portion 124, a second curved connector portion 126, and a coupling member 128 as is best shown in FIG. 23. The first connector portion 124 may have a plurality of adjustment apertures 130 defined therein while the second connector portion 126 similarly has a plurality of adjustment apertures 132 defined therein.

The surgically implantable instrumentation of spinal system 400 that has been described above, including the cranial plate member 24 the connection members 313, 413 and the vertebral plate 303 may alternatively be fabricated from a bioabsorbable material that progressively loses its strength and mass over time as it is absorbed into the human body. The ideal bioabsorbable material would have a composition that would retain sufficient strength for a sufficient period of time for adequate bone fusion and bone mass to develop so that the first and second bone forming material based structural members 27, 29 would provide adequate structural strength to maintain the fusion of the human occipitocervical junction at all times and under all foreseeable circumstances.

Figure 24:
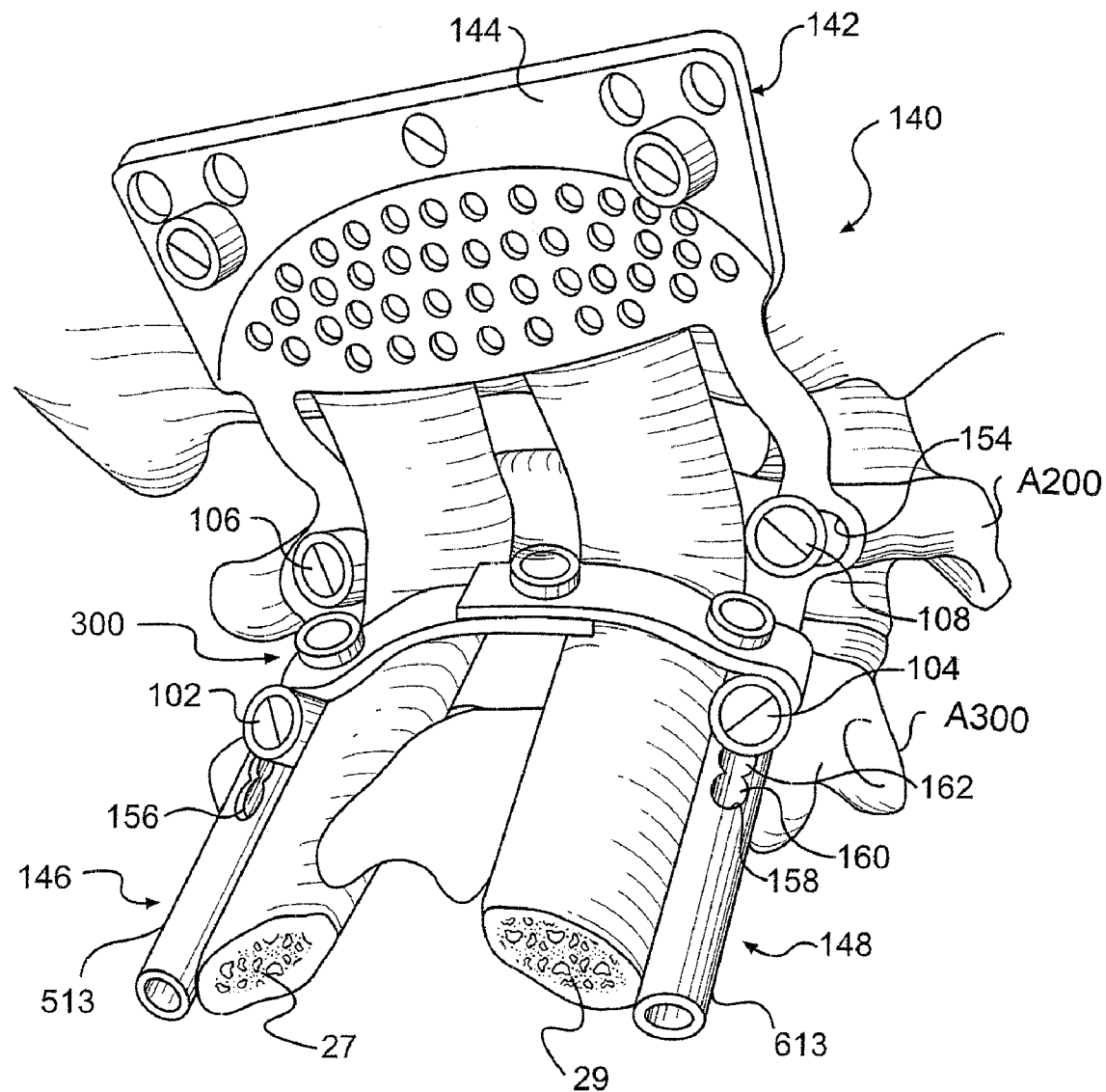
FIG. 24 is a perspective view showing another embodiment of the invention.

Referring now to FIG. 24, a occipital connection system 140 that is constructed according to an alternative embodiment of the invention includes an integrated fixation member 142 having a cranial plate member 144 and first and second appendages 146, 148 that are integral and preferably unitary with the cranial plate member 144. The appendages 146, 148 would intimately relate to the posterior arch A3 of the C1 vertebra A200, the lateral mass A4 of the C2, C3 vertebrae and any of the lower vertebrae. The goal of the monolithic design would be to simplify and increase the efficiency of application and stabilization of the device to the craniospinal junction.

Cranial plate member 144 is preferably constructed identically to the plate portion described above with reference to the previously described embodiment except as is described otherwise herein. The first and second appendages 146, 148 are preferably rigid and in the preferred embodiment are fabricated from a pair of generally parallel extending connection members 513, 613. Appendages 146, 148 are preferably preformed as described above with reference to the first embodiment of the invention so as to be bent at an angle reflecting the corrected reduction of the angle (α angle, FIG. 20) between the cranium and that of the spine, which in the preferred embodiment this will be pre-set within a range of about 75° to about 90°. Accordingly, the first and second integrated appendages 146, 148 are contoured to ensure a postoperative craniospinal relationship that confers a clivo-axial angle (the angle between the dorsum of the second cervical vertebra and the dorsum of the clivus) approaching about 155-165° and more preferably about 155-165°. Simultaneously, the degree of ventral brainstem compression should be rendered zero, by virtue of the reduction of angulation between the cranium and spine, and in some cases by the posterior translation of cranium upon spine.

In addition, the integrated appendages 146, 148 preferably incorporate a pre-established rise option (the α rise, described above with reference to FIG. 20), to accommodate the non-linearity of the level of the posterior arch A3 of the C1 vertebra A200 to the surface of the lamina A16 of the C2 vertebra A300 and lateral mass A4 of the C3 vertebra. The presence of the pre-established a rise will allow the integrated appendages 146, 148 to contact the C1 and C2 laminae A16, as shown in FIG. 24.

Another advantageous feature of the embodiment of the invention that is depicted in FIG. 24 is the provision of adjustment slots 156, 158 in the first and second appendages 146, 148, respectively, to permit positional adjustment of the integrated fixation member 142 with respect to the pedicle screws 102, 104 that are used to secure the first and second appendages 146, 148, respectively, to the C2 vertebrae. As FIG. 24 shows, adjustment slot 158 as well as adjustment slot 156 may include a plurality of prepositioned apertures or adjustment holes 160, 162 to permit indexing of the pedicle screw 104 within the appendage 148 or variability of screw purchase.

Likewise, adjustment slots 154 may be provided in the respective portions of the first and second appendages 146, 148 that are constructed and arranged to be secured to the C1 vertebrae A200 by pedicle screws 106, 108. This portion of the appendages 146, 148 is may be constructed so as to be slightly flared at the C1 vertebrae A200 to allow lateral variability.

As may be visualized from viewing FIG. 24, several possibilities of latitude are offered for the screw heads at the C1 vertebra A200, and several options for the screw heads of C2 are also available. The appendages 146, 148 may be solid, tubular, porous or even a metallurgically bonded porous metal coating that is constructed and arranged to encompass and contain bone graft material, such as TRABECULAR METAL™ by Zimmer Inc. of Warsaw, Ind.

An exemplary method for achieving occipitocervical fusion using spinal system 400 and attachment system 300 of the present invention will now be described. A patient is first positioned prone with a Mayfield pin headrest in an appropriate sterile surgical environment. The posterior cranium (subocciput) will then be surgically exposed.

The suboccipital bone will then preferably be lightly drilled or sculpted in order to create a flat and even surface for the positioning of the cranial plate member 24. The cranial plate member 24 will then be aligned with the long axis of the patient's body and will be positioned symmetrically about the midline axis, so that the central screw hole 40 is preferably bisected by the midline axis of the patient's cranium as viewed in rear elevation. The center of the central screw hole 40 will then be marked on the cranium, and the cranial plate member 24 will be removed.

A central hole will then be surgically drilled in the cranium, preferably to a depth of 5-10 mm. using a high speed drill, then by a conventional surgical hand drill to complete the drilling, preferably to a total depth of between about 8 mm to about 12 mm. The screw hole will be tapped to a depth that is about 1 mm longer than the screw to be used. For example, for a 10 mm screw, tap to 11 mm depth. The cranial plate member 24 will then be repositioned on the midline.

The central cortical screw 42 will then be inserted into the tapped hole and tightened, lagging down the cranial plate member 24 to achieve solid fixation.

The left C1 and C2 screws 102, 106 will then be respectively inserted into the C1 and C2 vertebral bodies as is best shown in FIGS. 14 and 21.

The left pre-contoured connection member 313 is loosely positioned within the first clamp 302 of the vertebral plate 303 and is secured to the left C1 and C2 screws 102, 106.

The triple screw position for the first connector assembly 62 that best aligns with the pre-contoured occipito-cervical connection member 313 is then selected. The triple screw purchase selected is then drilled in the cranium. The lateral screw purchase may then be tapped if it is not been pre-threaded. The triple screw 70 is inserted.

The same operation is performed, again choosing the most appropriate position for the triple screw 70 for the second system fastener 412.

The Mayfield headholder is then released, and an open reduction of the craniocervical junction is performed under fluoroscopy and under direct inspection. It is ensured that the abnormal angulation (kyphosis) of the craniospinal angle, and any abnormal translation of the skull is reduced, and that there is no rotation or lateral bending and no subluxation at lower spinal levels. The head-holder is then relocked.

The clivioaxial angle is then measured with the goal of achieving an optimal clivioaxial angle of 150° to 165°.

The connection members 313, 413 are then placed into the triple screws 70 within the respective system fastener 312, 412 and the hex nuts 82 are placed over the screws 70 and tightened.

The exposed suboccipital bone, the posterior arch A3 of the C1 vertebra A200 and the lamina A16 and facet joints A22 of the C2 vertebra A300 are then surgically decorticated.

The first portions 31, 27 of the first and second bone forming material based structural member 27, 29 are then inserted into the graft accommodation space 32 that is defined between the cranial plate member 24 and the cranium, as is best shown in FIG. 15. The cephalad part of the bone forming material based structural member should be fashioned to fit precisely and under pressure beneath the flange 25 of the cranial plate member 24. In some embodiments, the caudal edge 26 of the cranial plate member 24 may now be bent down towards the cranium to further compress the graft. The caudal end of the graft should lie on the decorticated C1 and C2 vertebrae (and lower levels where indicated) dorsal elements.

The graft loading vertebral plate 303 is then positioned to hold down, under pressure, the portions of the first and second bone forming material based structural members 27, 29 that are positioned over and against the C1 and C2 vertebrae dorsal elements. This is best illustrated in FIGS. 21-22.

The fasteners 302, 402 are then tightened on the vertebral plate 303.

Demineralized bone matrix may then be applied to the fusion areas and more cancellous bone may be applied to complete the fusion. A layered wound closure is then performed conventionally over a drain.

A method according to an alternative embodiment of the invention would utilize the integrated fixation member 142 that is depicted in FIG. 24. In this method, the steps may be slightly reordered. First, placement of the screws into the lateral mass A4 or posterior arch A3 of the C1 vertebra A200 and into the lateral mass A4 or pedicle A14 of the C2 vertebra A300, or into the lateral masses of the lower cervical or thoracic vertebrae would be performed.

Second the monolithic construct including the cranial plate member 144 and the integrated appendages 146, 148, which are surrogates for the rods 56 and 58 described with reference to the first embodiment of the invention, is applied over the screw heads.

Third, the craniospinal reduction is performed.

Fourth, the cranial plate member 144 is screwed to the skull with the central screw 42. The top loading nuts 106, 108 are then tightened down over the screw heads of the vertebral screws.

In all other respects, this method is identical to the method first described above.

Several embodiments of the present invention have been described herein. Nevertheless, it will be understood that various modifications may be made without departing form the spirit and scope of the invention. Accordingly, other embodiments are within the scope of the following claims.

What is claimed is:

1. An occipitocervical stabilization system comprising:
  a cranial plate;
  two rod members operatively associated with the cranial plate to enable stabilization of an occipitocervical junction;
  a vertebral plate positioned between and attached to the two rod members, wherein the vertebral plate comprises a first aperture;
  a clamp having a curved surface adapted to surround an edge of a bone member, wherein the clamp comprises:
    a first member adapted to engage a first surface of said bone member,
    wherein the first member comprises a second aperture; and
    a second member adapted to engage a second surface of said bone member; and
  a first fastener, wherein said first fastener is positioned through said first and second apertures to secure said vertebral plate and said clamp to said bone member, wherein the vertebral plate presses against a surface of said clamp when said first fastener is positioned to secure said clamp to said bone member and wherein the clamp is operatively associated with the vertebral plate to enable stabilization of the occipitocervical junction.

2. The system of claim 1, wherein the bone member is a posterior region of a vertebra, the first surface is a dorsal surface of the posterior region of the vertebra and the second surface is a ventral surface of the posterior region of the vertebra and wherein the clamp is sized and adapted to surround an edge of the posterior region of the vertebra positioned between the dorsal surface and the ventral surface of the vertebra.

3. The system of claim 2, wherein said first fastener engages one of the two rod members and connects said rod member to said at least one clamp and said vertebra.

4. The system of claim 3, wherein said first fastener is a triple screw member comprising a first threaded portion for engaging said posterior region of the vertebra, a second portion for engaging said clamp and a third portion for engaging said rod member.

5. The system of claim 2, wherein said posterior region is selected from the group consisting of: a posterior arch of a cervical vertebra and a lamina.

6. The system of claim 5, wherein said vertebral plate spans a substantial length of said posterior region and has a curvature corresponding to said dorsal surface of said posterior region.

7. The system of claim 2, wherein said second member comprises a third aperture vertically aligned with said first and second apertures.

8. The system of claim 2, wherein said clamp has a configuration selected from the group consisting of: a U shape, a semi-circular shape and a collar.

9. The system of claim 2, wherein said vertebral plate comprises a plurality of apertures, wherein at least two of said plurality of apertures have a different dimension.

10. The system of claim 2, wherein said first fastener is selected from the group consisting of: a screw, a rivet and a bolt.

11. The system of claim 2, wherein the first fastener comprises a locking mechanism.

12. The system of claim 2, further comprising:
a second fastener comprising a third aperture and a locking mechanism, wherein one of said rod members is retained in said third aperture by said locking mechanism, and wherein said second fastener is attached to said vertebral plate.

13. The system of claim 1, wherein said curved surface of said clamp has a curvature of about 4 radians.

14. An occipitocervical stabilization system comprising:
an U shaped cranial plate;
a vertebral plate having a contour conforming to a portion of a vertebra;
two clamps operatively associated with the cranial plate so as to enable stabilization of an occipitocervical junction, wherein the clamps are adapted to surround an edge of the vertebra and wherein each of the clamps comprises:
a first member adapted to engage a first surface of said vertebra,
wherein the first member comprises a first aperture; and
a second member adapted to engage a second surface of said vertebra,
wherein said vertebral plate is integral with and forms a continuous horizontal extension of said first members of each of said clamps;
a first fastener securing the first clamp to the vertebra and the cranial plate; and
a second fastener securing the second clamp to the vertebra and the cranial plate.

15. The system of claim 14, wherein said clamps are spaced apart from one another and integrally formed with opposite ends of said vertebral plate such that said vertebral plate is positioned between said two clamps.

16. The system of claim 14, wherein the cranial plate comprises:
a cranial plate member adapted to be attached to a cranium; and
two appendages extending from the cranial plate member and adapted to be secured to the vertebra.

* * * * *